United States Patent
Gomi et al.

(10) Patent No.: US 10,269,153 B2
(45) Date of Patent: Apr. 23, 2019

(54) INFORMATION PROCESSING APPARATUS PROVIDING INFORMATION RELATED TO SKIN STATE OF USER

(71) Applicant: SONY CORPORATION, Tokyo (JP)

(72) Inventors: Shinichiro Gomi, Tokyo (JP); Yusuke Nakamura, Kanagawa (JP); Natsuki Kimura, Tokyo (JP); Akari Hoshi, Tokyo (JP)

(73) Assignee: SONY CORPORATION, Tokyo (JP)

(*) Notice: Subject to any disclaimer, the term of this patent is extended or adjusted under 35 U.S.C. 154(b) by 54 days.

(21) Appl. No.: 14/915,190

(22) PCT Filed: Aug. 15, 2014

(86) PCT No.: PCT/JP2014/071467
§ 371 (c)(1),
(2) Date: Feb. 26, 2016

(87) PCT Pub. No.: WO2015/029801
PCT Pub. Date: Mar. 5, 2015

(65) Prior Publication Data
US 2016/0210764 A1     Jul. 21, 2016

(30) Foreign Application Priority Data
Aug. 30, 2013   (JP) ................................. 2013-179602

(51) Int. Cl.
*G06T 11/20*   (2006.01)
*A61B 5/00*   (2006.01)
*A45D 44/00*   (2006.01)
(Continued)

(52) U.S. Cl.
CPC ............ *G06T 11/206* (2013.01); *A45D 44/00* (2013.01); *A45D 44/005* (2013.01); *G06Q 10/10* (2013.01);
(Continued)

(58) Field of Classification Search
CPC . G06T 11/206; G06T 2210/41; G06F 3/0481; G06F 17/246; G06Q 30/06;
(Continued)

(56) References Cited

U.S. PATENT DOCUMENTS

2008/0194928 A1* 8/2008 Bandic ................... G16H 15/00
                                                                    600/306
2009/0312998 A1* 12/2009 Berckmans ......... G06F 19/3437
                                                                    703/11
(Continued)

FOREIGN PATENT DOCUMENTS

| CN | 106491120 A | * | 3/2017 |
|---|---|---|---|
| JP | HEI 07-231883 A | | 9/1995 |
| JP | HEI 07-289524 A | | 11/1995 |
| JP | 2002-207827 A | | 7/2002 |
| JP | 2003-144393 A | | 5/2003 |
| JP | 2007-152084 A | | 6/2007 |

Primary Examiner — Chante E Harrison
(74) Attorney, Agent, or Firm — Chip Law Group

(57) ABSTRACT

The present technology relates to an information processing apparatus, an information processing method, and an information processing system, which are capable of presenting useful information to a user. A correlation calculation unit finds correlation between a plurality of pieces of first information input by a user and one or more pieces of second information obtained as values by measuring the user. A specific information extraction unit extracts, as specific first information, at least first information highest in correlation with the second information among the plurality of pieces of first information. A display unit performs adjustment for simultaneously displaying the specific first information and the second information. The present technology can be applied to an information processing apparatus analyzing a skin state of a user, for example.

14 Claims, 21 Drawing Sheets

(51) Int. Cl.
*G06Q 10/10* (2012.01)
*G06Q 50/22* (2018.01)

(52) U.S. Cl.
CPC ........ *A45D 2044/007* (2013.01); *A61B 5/442* (2013.01); *G06Q 50/22* (2013.01); *G06T 2210/41* (2013.01)

(58) Field of Classification Search
CPC ........ G06Q 40/04; G06Q 50/22; G06Q 10/10; A61B 5/441; A61B 5/442; A45D 44/00; A45D 44/005; A45D 2044/007; G16H 10/20
USPC .............................................. 345/440, 440.2
See application file for complete search history.

(56) References Cited

U.S. PATENT DOCUMENTS

| | | | |
|---|---|---|---|
| 2010/0185064 A1* | 7/2010 | Bandic | A61B 5/0059 600/306 |
| 2012/0290266 A1* | 11/2012 | Jain | G16H 40/63 702/187 |
| 2015/0120205 A1* | 4/2015 | Jeon | A61B 5/015 702/19 |
| 2015/0186609 A1* | 7/2015 | Utter, II | A61B 5/0022 600/301 |
| 2016/0005320 A1* | 1/2016 | deCharms | G09B 5/065 434/236 |

* cited by examiner

FIG. 9

| LIFESTYLE HABIT | | |
|---|---|---|
| SLEEP | 6 HOURS | |
| | SLEEPING TIME [ ▼ ] ~ [ ▼ ] | |
| DEGREE OF COMFORTABLE SLEEP | 😀 🙂 🙂 😟 😴 | |
| MEAL | BREAKFAST | LUNCH | DINNER |
| DEFECATION | REFRESHED | NORMAL | STIFFENED |
| | DIARRHEA | CONSTIPATION | |
| EXERCISE | ✓ | |
| | 🚶 🏃 🚴 🙆 🧘 | |
| | 💃 🏊 🎾 🏌 OTHERS | |
| | HOURS [ ▼ ] | |
| | LOAD | |
| | HIGH | NORMAL | LOW |
| BATHING | HOT SPRING | BATHTUB | SHOWER |
| | FOOT BATH | NOT BATHING | |
| MENSTRUATION | ✓ | |
| BASAL BODY TEMPERATURE | [ ] °C | |

~500

INFORMATION PROCESSING APPARATUS PROVIDING INFORMATION RELATED TO SKIN STATE OF USER

TECHNICAL FIELD

The present technology relates to an information processing apparatus, an information processing method, and an information processing system, and particularly to an information processing apparatus, an information processing method, and an information processing system, which are capable of presenting useful information to a user.

BACKGROUND ART

Recently, the information technology has been actively introduced also into a beauty field, and there are proposed various kinds of technology for presenting a skin state or providing a beauty advice to a user, for example.

For example, Patent Literature 1 discloses the technology of analyzing a skin state using a face image obtained by imaging a user, accumulating measurement results obtained by the analysis in association with user information or measurement dates, and presenting the measurement results of the measurement dates for each user (see FIG. 10 and FIG. 14, for example).

Moreover, for example, Patent Literature 2 discloses the technology of presenting a beauty advice in accordance with a result of a user's state input by the user (see FIG. 5 and FIG. 6, for example).

CITATION LIST

Patent Literature

Patent Literature 1: JP 2007-152084A
Patent Literature 2: JP 2002-207827A

SUMMARY OF INVENTION

Technical Problem

Note that the technology disclosed in Patent Literature 1 represents a measurement result for each measurement date, and does not represent the relation with a user's state input by the user. Moreover, the technology disclosed in Patent Literature 2 represents a beauty advice in accordance with a user's state input by the user, and does not represent the relation with a measurement result obtained by measuring the user.

That is, in the technology disclosed in these patent literatures, the input data indicating the subjective state of the user is not associated with the measurement data indicating the objective state of the user. Thus, the actual feeling of the user is not connected to the measurement data, and it is not considered that the useful information is presented to the user.

The present technology is made in view of such a situation, and aims at presenting useful information to a user by associating input data indicating the subjective state of the user with measurement data indicating the objective state of the user.

Solution to Problem

According to a first aspect of the present technology, there is provided an information processing apparatus including: a correlation calculation unit configured to find correlation between a plurality of pieces of first information input by a user and one or more pieces of second information obtained as values by measuring the user; a specific information extraction unit configured to extract, as specific first information, at least first information highest in correlation with the second information among the plurality of pieces of first information; and a display adjustment unit configured to perform adjustment for simultaneously displaying the specific first information and the second information.

The display adjustment unit may display at least a value of the specific first information when a measurement result indicated by the second information indicates a most preferable state.

The display adjustment unit may display the specific first information and the second information in a first display form when correlation between the specific first information and the second information is positive correlation, and display the specific first information and the second information in a second display form when the correlation between the specific first information and the second information is negative correlation.

The display adjustment unit may display the specific first information and the second information in time series.

The display adjustment unit may highlight a value of the second information when a change amount in a given time unit of the second information in time series exceeds a given threshold.

The display adjustment unit may perform different highlighting between when the change amount of the second information is a positive value and when the change amount of the second information is a negative value.

The display adjustment unit may display a value of the specific first information when a change amount in a given time unit of the second information in time series exceeds a given threshold.

The specific information extraction unit may extract, as the specific first information, first information having no correlation with the second information among the plurality of pieces of first information.

The specific information extraction unit may extract, as the specific first information, N pieces (N is an integer equal to or more than 2) of first information high in correlation with the second information among the plurality of pieces of first information.

The specific first information may be N pieces of first information higher or lower in correlation among the plurality of pieces of first information high in correlation with the second information.

The display adjustment unit may display the specific first information and the second information in time series.

The display adjustment unit may display the specific first information and the second information by line graphs on a plane with a vertical axis indicating score values of the information and a horizontal axis as a time axis.

The display adjustment unit may display the specific first information and the second information by a scatter diagram with a vertical axis and a horizontal axis indicating score values of the information.

The specific information extraction unit may extract, as the specific first information, predetermined first information or first information specified by a user among the plurality of pieces of first information.

The first information may be information obtained by inputting a current state of the user. The second information may be information indicating a measurement result of a skin state of the user.

An input unit configured to input the first information indicating the current state of the user; and a display unit configured to simultaneously display the specific first information indicating the current state of the user and the second information indicating the skin state of the user that are adjusted by the display adjustment unit may be further included.

A measurement unit configured to measure the skin state of the user may be further included.

An information processing method of the first aspect of the present technology corresponds to the information processing apparatus of the first aspect of the present technology.

According to the first aspect of the present technology, in an information processing apparatus and an information processing method, correlation between a plurality of pieces of first information input by a user and one or more pieces of second information obtained as values by measuring the user is found, at least first information highest in correlation with the second information among the plurality of pieces of first information is extracted as specific first information, and adjustment for simultaneously displaying the specific first information and the second information is performed.

According to a second aspect of the present technology, there is provided an information processing system including: a terminal device; a measurement device connected to the terminal device; and an information processing apparatus configured to perform communication with the terminal device through a network. The measurement device includes a measurement unit configured to measure a user. The terminal device includes an input unit configured to be operated by the user, and a display unit configured to display various kinds of information. The information processing apparatus includes a correlation calculation unit configured to find correlation between a plurality of pieces of first information input by operation of the user on the input unit and one or more pieces of second information obtained as values by measuring the user by the measurement unit, a specific information extraction unit configured to extract, as specific first information, at least first information highest in correlation with the second information among the plurality of pieces of first information, and a display adjustment unit configured to perform adjustment for simultaneously displaying the specific first information and the second information. The display unit simultaneously displays the specific first information and the second information that are adjusted by the display adjustment unit.

In an information processing system according to the second aspect of the present technology, correlation between a plurality of pieces of first information input by a user and one or more pieces of second information obtained as values by measuring the user is found, first information highest in correlation with the second information is extracted, as specific first information, among the plurality of pieces of first information, and adjustment for simultaneously displaying the specific first information and the second information is performed.

Advantageous Effects of Invention

According to the first aspect and the second aspect of the present technology, it is possible to present useful information to a user. Note that the effects described herein are not limited, and any effects described in the present disclosure may be exerted.

BRIEF DESCRIPTION OF DRAWINGS

FIG. 9 is a diagram illustrating a display example of an input screen.

DESCRIPTION OF EMBODIMENTS

Hereinafter, the embodiments of the present technology will be described with reference to the appended drawings.
<First Embodiment>
<Configuration of Skin Analysis System>

Figure 1:
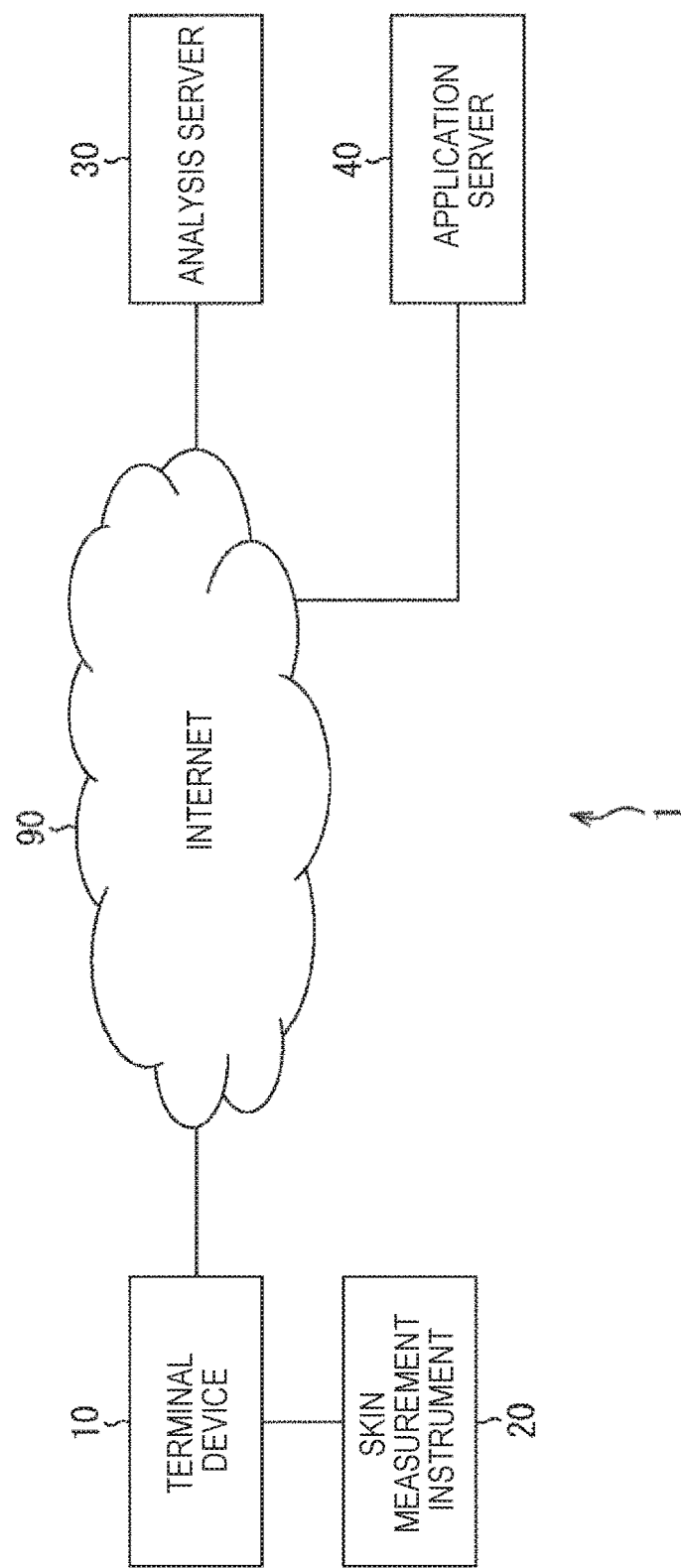
FIG. 1 is a diagram illustrating a configuration of an embodiment of an information processing system to which the present technology is applied.

FIG. 1 is a diagram illustrating a configuration of an embodiment of an information processing system to which the present technology is applied.

A skin analysis system 1 of FIG. 1 analyzes the relation between input data indicating the current state (actual feeling) of a user and measurement data indicating a measurement result of the state of user's skin, and presents information combining such data to a user in a given display form.

As illustrated in FIG. 1, the skin analysis system 1 includes a terminal device 10, a skin measurement instrument 20, an analysis server 30, and an application server 40. Here, the terminal device 10 and the skin measurement instrument 20 are connected through a cable supporting a given standard. Moreover, the terminal device 10 and the analysis server 30 and the application server 40 are connected to each other through the Internet 90. Note that the terminal device 10 and the skin measurement instrument 20 may be connected by wire or connected by given wireless communication, for example. Moreover, the Internet 90 is an example of a network, and the connection may be through another network such as a local area network (LAN), for example.

The terminal device 10 is an electronic device such as a mobile communication terminal including a smartphone and a mobile information device including a tablet-type computer. The terminal device 10 has a touch panel in which a touch sensor and a display unit are integrated and performs, when input operation is performed with a user's finger, and the like, various kinds of processing in accordance with the input operation. Moreover, the terminal device 10 accesses the application server 40 through the Internet 90 and downloads an application for skin analysis. The terminal device 10 acquires input data in accordance with input operation of the user while the application for skin analysis is being executed, and transmits the input data to the analysis server 30 through the Internet 90.

The skin measurement instrument 20 images a subject including a user's face and acquires measurement data of the skin obtained by analyzing image data of the face image. The skin measurement instrument 20 outputs the measurement data to the terminal device 10 through the cable. The terminal device 10 acquires the measurement data input from the skin measurement instrument 20 and transmits the measurement data to the analysis server 30 through the Internet 90.

The analysis server 30 receives the input data and the measurement data transmitted from the terminal device 10 through the Internet 90. The analysis server 30 calculates the correlation between the input data and the measurement data from the analysis server 10, and generates display data having a display form in accordance with the calculation result. Here, for example, at least input data highest in correlation with the measurement data is extracted as specific input data among a plurality of pieces of input data, and display data for simultaneously displaying the specific input data and measurement data is generated. The analysis server 30 transmits the display data to the terminal device 10 through the Internet 90.

The terminal device 10 receives the display data transmitted from the analysis server 30 through the Internet 90. The terminal device 10 simultaneously displays the specific input data and the measurement data on the display unit in a display form in accordance with the display data from the analysis server 30.

Note that although the configuration of FIG. 1 illustrates an example in which only one terminal 10 is connected to the Internet 90, for convenience of explanation, a plurality of terminal devices 10 having downloaded the application for skin analysis from the application server 40 are actually connected to the Internet 90 to access the analysis server 30. Moreover, the application for skin analysis may not be downloaded from the application server 40 but may be preliminarily installed in the terminal device 10.

The skin analysis system 1 is configured in the manner described above.

(Configuration of Terminal Device)

Figure 2:
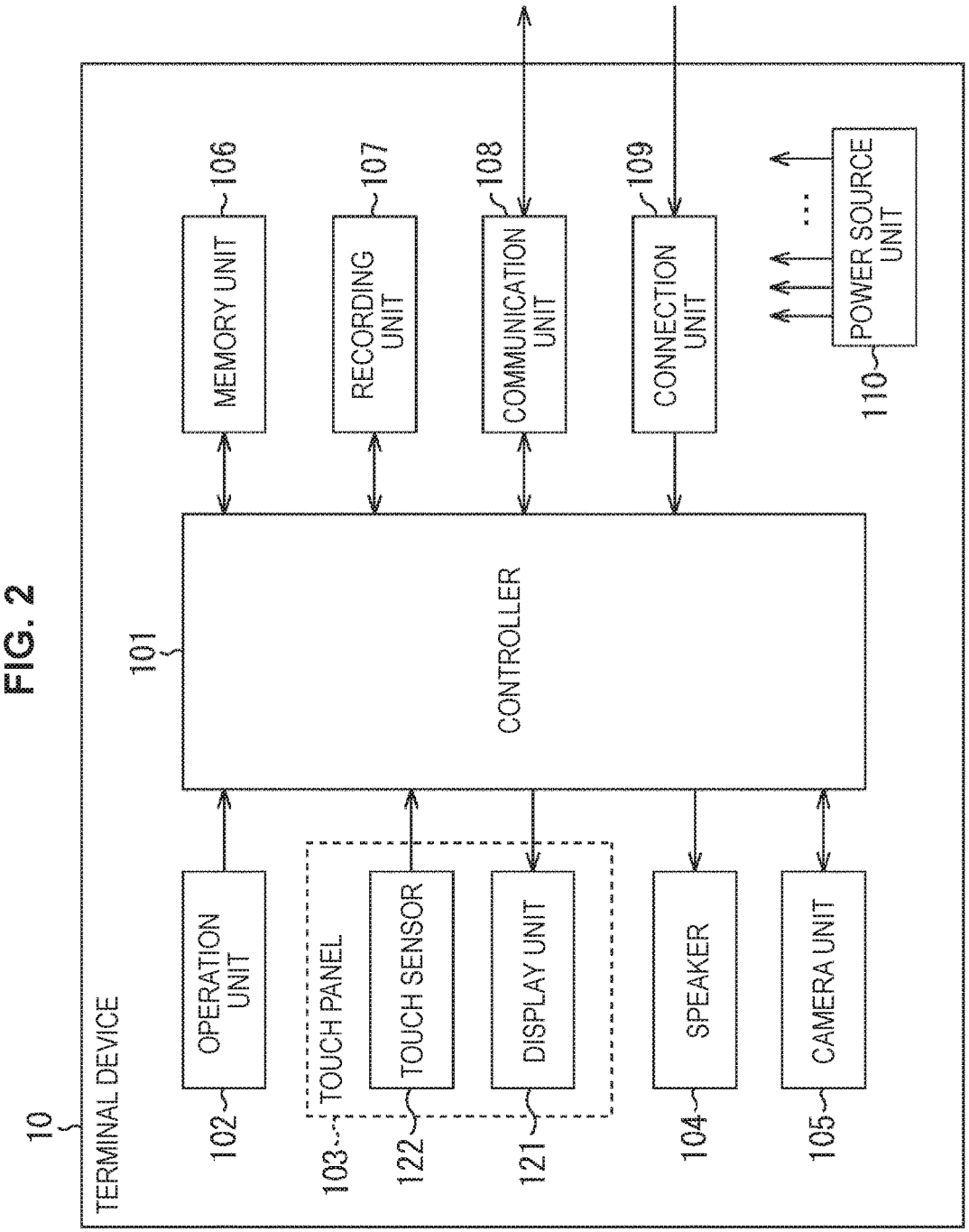
FIG. 2 is a diagram illustrating a configuration of an embodiment of a terminal device to which the present technology is applied.

FIG. 2 is a diagram illustrating a configuration of an embodiment of a terminal device to which the present technology is applied.

As illustrated in FIG. 2, the terminal device 10 of FIG. 1 includes a controller 101, an operation unit 102, a touch panel 103, a speaker 104, a camera unit 105, a memory unit 106, a recording unit 107, a communication unit 108, a connection unit 109, and a power source unit 110.

The controller 101 controls the operation of each unit of the terminal device 10. The operation unit 102 is a button, and the like provided on the terminal device 10, and supplies an operation signals to the controller 101 in accordance with user's operation. The controller 101 controls the operation of each unit in accordance with operation signals from the operation unit 102.

The touch panel 103 includes a display unit 121 and a touch sensor 122 superimposed on a screen of the display unit 121. The display unit 121 includes a liquid crystal display (LCD) and the like, and displays various kinds of information in accordance with the control from the controller 101. Moreover, the touch sensor 122 detects input operation performed on the touch panel 103 by a user, together with a position on the touch panel 103 where such operation has been operated, and supplies the detection signals to the controller 101.

Here, the input operation detected by the touch sensor 122 includes operation of bringing a user's finger into contact with a surface of the touch panel 103, operation of moving the user's finger while it is kept in contact with the surface of the touch panel 103, and operation of separating the user's finger from the surface of the touch panel 103, for example.

The speaker 104 outputs sound corresponding to sound signals in accordance with the control from the controller 101. The camera unit 105 is a camera including a solid state imaging device such as a complementary metal oxide semiconductor (CMOS) image sensor. The camera unit 105 supplies image data obtained by imaging a subject and performing given imaging processing to the controller 101, in accordance with the control from the controller 101.

The memory unit 106 temporarily retains various kinds of data in accordance with the control from the controller 101. The recording unit 107 includes a removable memory card or hard disk drive (HDD), and the like. The recording unit 107 records various kinds of data in accordance with the control from the controller 101.

The communication unit 108 performs communication with various servers such as the analysis server 30 through the Internet 90 in accordance with the control from the controller 101, and exchanges various kinds of data. For example, the communication unit 108 accesses the application server 40 through the Internet 90 and downloads the application for skin analysis. The downloaded application for skin analysis is recorded in the recording unit 107. Moreover, when the user performs input operation on the touch panel 103 while the application for skin analysis is being executed, the communication unit 108 transmits input data in accordance with detection signals from the touch sensor 122 to the analysis server 30 through the Internet 90. However, the input operation of the user may be performed through the operation unit 102.

The connection unit 109 is connected to the skin measurement instrument 20 through the cable supporting a given standard. The connection unit 109 supplies the measurement data from the skin measurement instrument 20 to the communication unit 108, in accordance with the control from the controller 101. The communication unit 108 transmits the measurement data from the skin measurement instrument 20 to the analysis server 30 through the Internet 90.

Moreover, the communication unit 108 receives display data transmitted from the analysis server 30 through the Internet 90 and supplies the display data to the display unit 121, in accordance with the control from the controller 101. Thus, the specific input data and the measurement data are simultaneously displayed on the display unit 121 in a display form in accordance with the display data.

The power source unit 110 supplies power supply power obtained from a storage battery or an external power supply to each unit of the terminal device 10 including the controller 101.

As described above, when the application for skin analysis is activated, the terminal device 10 transmits the input data and the measurement data to the analysis server 30 through the Internet 90, thereby simultaneously displaying the specific input data and the measurement data in a display form in accordance with the analysis result by the analysis server 30.

(Configuration of Skin Measurement Instrument)

Figure 3:
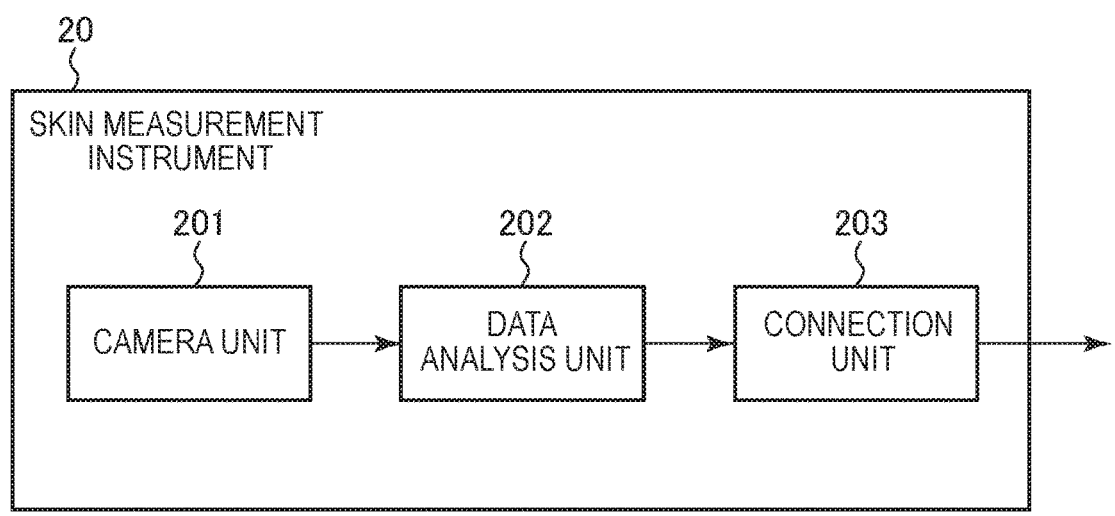
FIG. 3 is a diagram illustrating a configuration of an embodiment of a measurement device to which the present technology is applied.

FIG. 3 is a diagram illustrating a configuration of an embodiment of a measurement device to which the present technology is applied.

As illustrated in FIG. 3, the skin measurement instrument 20 of FIG. 1 includes a camera unit 201, a data analysis unit 202, and a connection unit 203.

The camera unit 201 is a camera including a solid state imaging device such as a CMOS image sensor. The camera unit 201 supplies image data obtained by imaging a subject including a user's face and performing given image processing to the data analysis unit 202.

The data analysis unit 202 performs given skin analysis processing on the image data supplied from the camera unit 201 and acquires skin measurement data. The data analysis unit 202 supplies the skin measurement data obtained by the analysis to the connection unit 203. Here, as skin measurement data, there is acquired information related to the skin state such as the state of pores, stains, and texture, for example, which is obtained by analyzing an image of a user's face.

The connection unit 203 is connected to the terminal device 10 through the cable supporting a given standard. The connection unit 203 outputs the measurement data supplied from the data analysis unit 202 to the terminal device 10 through the cable.

As described above, when the application for skin analysis is activated in the terminal device 10, the skin measurement instrument 20 outputs the measurement data obtained by measuring user's skin to the terminal device 10.

(Configuration of Analysis Server)

Figure 4:
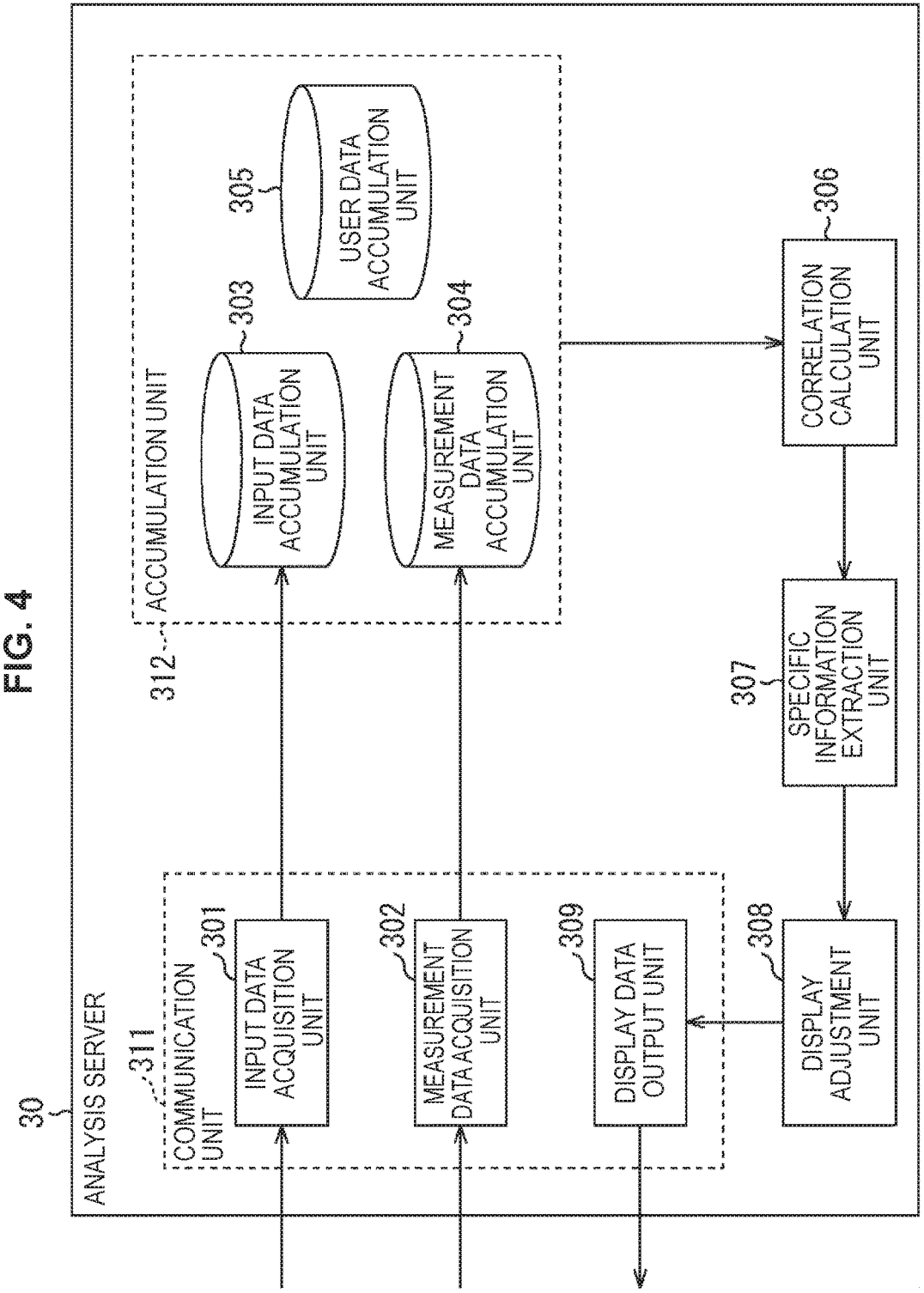
FIG. 4 is a diagram illustrating a configuration of an embodiment of an information processing apparatus to which the present technology is applied.

FIG. 4 is a diagram illustrating a configuration of an embodiment of an information processing apparatus to which the present technology is applied.

As illustrated in FIG. 4, the analysis server 30 of FIG. 1 includes an input data acquisition unit 301, a measurement data acquisition unit 302, an input data accumulation unit 303, a measurement data accumulation unit 304, a user data accumulation unit 305, a correlation calculation unit 306, a specific information extraction unit 307, a display adjustment unit 308, and a display data output unit 309.

Here, the input data acquisition unit 301, the measurement data acquisition unit 302, and the display data output unit 309 form a part of a communication unit 311 performing communication with the terminal device 10 through the Internet 90. Moreover, the input data accumulation unit 303, the measurement data accumulation unit 304, and the user data accumulation unit 305 form a part of an accumulation unit 312 accumulating various kinds of data.

The input data acquisition unit 301 receives input data transmitted from the terminal device 10 through the Internet 90 and supplies the input data to the input data accumulation unit 303. The input data accumulation unit 303 sequentially accumulates the input data supplied from the input data acquisition unit 301.

The measurement data acquisition unit 302 receives measurement data transmitted from the terminal device 10 through the Internet 90 and supplies the measurement data to the measurement data accumulation unit 304. The measurement data accumulation unit 304 sequentially accumulates the measurement data supplied from the measurement data acquisition unit 302. Note that a data analysis unit (not illustrated) may be provided in the stage following the measurement data acquisition unit 302 to perform skin analysis processing on image data, instead of the data analysis unit 202 of the skin measurement instrument 20 of FIG. 3, and the measurement data obtained by such processing may be accumulated in the measurement data accumulation unit 304.

The user data accumulation unit 305 accumulates user data related to a user using the application for skin analysis. The user data is registered from the terminal device 10 through the Internet 90. Thus, the input data and the measurement data for each user are accumulated in time series in the input data accumulation unit 303 and the measurement data accumulation unit 304.

The correlation calculation unit 306 acquires a plurality of pieces of input data accumulated in the input data accumulation unit 303 and one or more pieces of measurement data accumulated in the measurement data accumulation unit 304 to find the correlation between the input data and the measurement data. The correlation calculation unit 306 supplies a calculation result of the correlation between the input data and the measurement data to the specific information extraction unit 307.

The specific information extraction unit 307 extracts at least input data highest in correlation with the measurement data among a plurality of pieces of input data, in accordance with the calculation result supplied from the correlation calculation unit 306. The specific information extraction unit 307 supplies the extracted input data to the display adjustment unit 308 as specific input data. Note that the specific information extraction unit 307 can extract, as specific input data, input data having no (low) correlation with the measurement data, predetermined input data, input data specified by the user, and the like. Moreover, a plurality of pieces of specific input data can be extracted.

The display adjustment unit 308 uses the specific input data and the measurement data supplied from the specific information extraction unit 307 to perform adjustment for simultaneously displaying the specific input data and the measurement data on the side of the terminal device 10, and supplies display data obtained as a result of the adjustment to the display data output unit 309.

The display data output unit 309 transmits the display data supplied from the display adjustment unit 308 to the terminal device 10 through the Internet 90.

As described above, the analysis server 30 analyzes the input data and the measurement data received from the terminal device 10 through the Internet 90, so that the terminal device 10 simultaneously displays the specific input data and the measurement data in a display form in accordance with the analysis result.

<Skin Analysis Processing>

Figure 6:
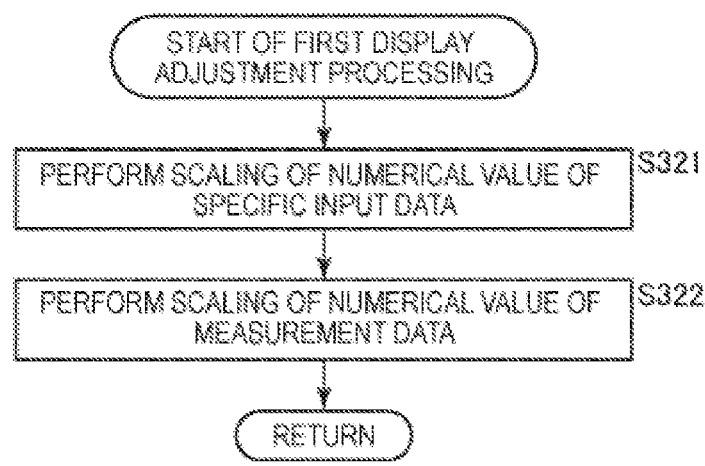
FIG. 6 is a flowchart for explaining first display adjustment processing.
Figure 7:
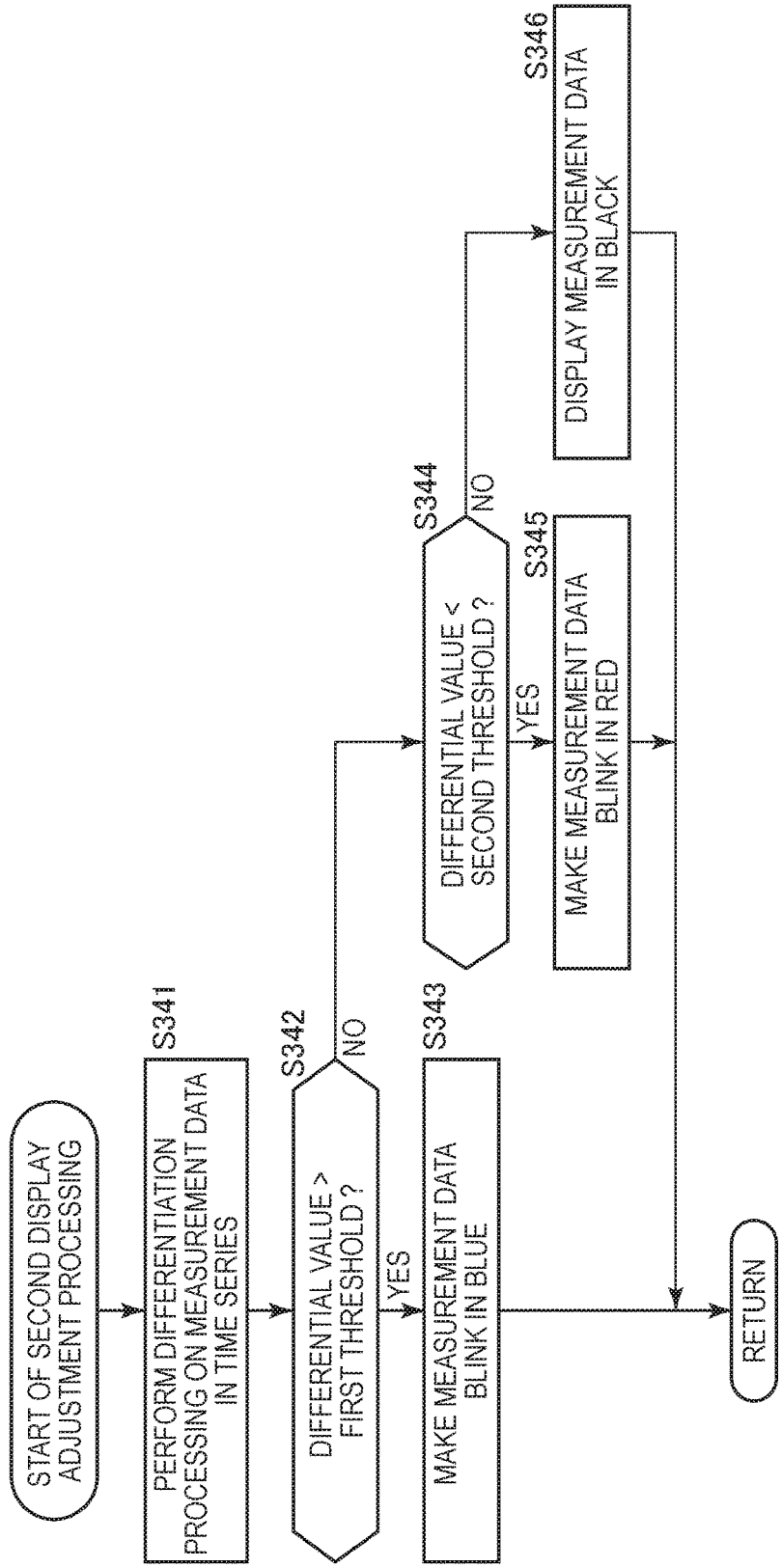
FIG. 7 is a flowchart for explaining second display adjustment processing.

Next, skin analysis processing performed by each device forming the skin analysis system 1 will be described with reference to the flowcharts of FIG. 5 to FIG. 7.

(Skin Analysis Processing)

Figure 5:
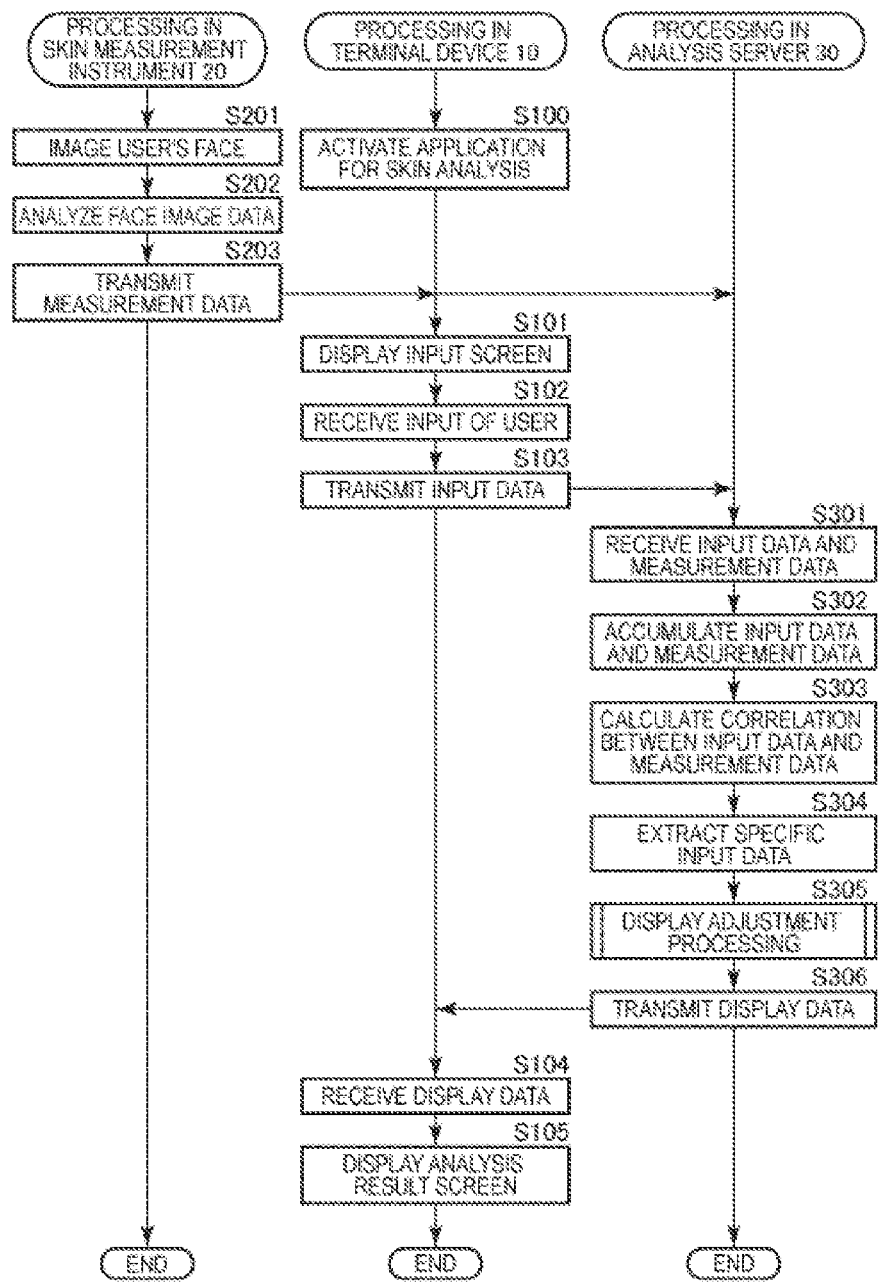
FIG. 5 is a flowchart for explaining skin analysis processing.

FIG. 5 is a flowchart for explaining skin analysis processing. The skin analysis processing is performed when a downloaded application for skin analysis is activated in the terminal device 10, for example (S100). Here, in the flowchart of FIG. 5, the terminal device 10 performs the processing of Steps S100 to S105, the skin measurement instrument 20 performs the processing of Step S201 to S203, and the analysis server 30 performs the processing of Step S301 to S306.

At Step S201, when a user has performed given operation, the camera unit 201 of the skin measurement instrument 20 images a subject including a use's face, and supplies image data obtained by such imaging to the data analysis unit 202. At Step S202, the data analysis unit 202 analyzes the image data of a face image imaged by the camera unit 201 and supplies skin measurement data obtained as a result of the analysis to the connection unit 203. In the skin analysis processing, there is obtained information related to the state of user's skin such as the state of pores, stains, and texture, for example.

At Step S203, the connection unit 203 outputs the measurement data from the data analysis unit 202 to the terminal device 10. In the terminal device 10, the measurement data from the skin measurement instrument 20 is input to the connection unit 109. Thus, the controller 101 controls the communication unit 108 to transmit the measurement data form the skin measurement instrument 20 to the analysis server 30 through the Internet 90.

Moreover, in the terminal device 10, when the application for skin analysis has been activated (S100), an input screen for inputting user's actual feeling is displayed on the display unit 121 (S101). At Step S102, the controller 101 controls the touch panel 103 to receive input operation of the user performed on the input screen displayed on the display unit 121. For example, on the input screen, there is displayed a graphical user interface (GUI) for inputting lifestyle habit such as sleep, diet, and exercise, and skincare habit such as skincare in addition to basic items such as feeling and a body condition (input screen 500 of FIG. 8 to FIG. 10 described later, for example).

At Step S103, the controller 101 controls the communication unit 108 to transmit input data in accordance with the input operation of the user on the input screen to the analysis server 30 through the Internet 90. Note that although the above description has been given assuming that the input data is transmitted after the measurement data is transmitted, the order of transmission of such data may be opposite or simultaneous.

At Step S301, the input data acquisition unit 301 and the measurement data acquisition unit 302 of the analysis server 30 receive the input data and the measurement data transmitted from the terminal device 10 through the Internet 90. Then, among the data received from the terminal device 10, the input data is accumulated in the input data accumulation unit 303, and the measurement data is accumulated in the measurement data accumulation unit 304 (S302).

At Step S303, the correlation calculation unit 306 calculates the correlation between the input data and the measurement data. Here, when the feeling and body condition, the number of times of meals, and the sleeping hours of the user are input as the input data, for example, the correlation between such input data and the skin state indicated by the measurement data is found. To be more specific, when a maximum value of the degree of correlation is 1, for example, the correlation between the feeling and body condition and the skin state is found to be 0.8, the correlation between the number of times of meals and the skin state is found to be 0.3, and the correlation between the sleeping hours and the skin state is found to be 0.7, for example.

At Step S304, the specific information extraction unit 307 extracts specific input data from a plurality of pieces of input data, in accordance with the calculation result of the correlation by the correlation calculation unit 306. For example, the specific information extraction unit 307 extracts, as specific input data, input data highest in correlation with the measurement data among a plurality of pieces of input data. In the case of the above-described example, the sleeping hours highest in correlation is extracted as specific input data, among the feeling and body condition, the number of times of meals, and the sleeping hours.

At Step S305, the display adjustment unit 308 performs display adjustment processing. In the display adjustment processing, the adjustment for simultaneously displaying the specific input data and the measurement data on the side of the terminal device 10 is performed, and display data in accordance with the adjustment result is generated. Note that the details of the display adjustment processing will be described later with reference to the flowcharts of FIG. 6 and FIG. 7.

At Step S306, the display data output unit 309 transmits the display data generated by the display adjustment unit 308 to the terminal device 10 through the Internet 90.

At Step S104, the controller 101 controls the controller 108 to receive the display data transmitted from the analysis server 30 through the Internet 90. At Step S105, the controller 101 displays, based on the display data from the analysis server 30, an analysis result screen in accordance with the display data on the display unit 121 (analysis result screen 600 of FIG. 11 to FIG. 18 described later, for example).

The above has described the skin analysis processing.

(First Display Adjustment Processing)

Next, the first display adjustment processing corresponding to Step S305 of FIG. 5 will be described with reference to the flowchart of FIG. 6.

At Step S321, the display adjustment unit 308 performs scaling of a numerical value of the specific input data. Moreover, at Step S322, the display adjustment unit 308 performs scaling of a numerical value of the measurement data.

For example, when the measurement data such as the state of pores, stains, and texture is evaluated in five grades, and the number of times of meals evaluated in three grades of breakfast, lunch, and dinner is extracted as specific input data, these evaluation scales are different. Thus, the display adjustment unit 308 multiplies the numerical value of the measurement data by ⅗ to match the evaluation scale. Moreover, regarding the input data that cannot be represented by evaluation in three grades or five grades, such as a basal body temperature, for example, the range between 35.0° C. to 37.5° C. is divided and represented in each 0.5° C. in accordance with the evaluation scale in five grades so as to match the scale.

When the processing at Step S322 is finished, the processing returns to Step S305 of FIG. 5 and the subsequent processing is performed.

As described above, in the first display adjustment processing, even when the evaluation scale is different between specific input data and measurement data or another kind of specific input data, the scaling of numerical values of the specific input data and the measurement data is performed to adjust display data and thus represent accurate correlation between such data, thereby presenting useful information to the user.

(Second Display Adjustment Processing)

Next, the second display adjustment processing corresponding to Step S305 of FIG. 5 will be described with reference to the flowchart of FIG. 7.

At Step S341, the display adjustment unit 308 performs differentiation processing on measurement data in time series. At Step S342, the display adjustment unit 308 determines whether the differential value obtained by the differentiation processing at Step S341 exceeds a first threshold.

When it is determined at Step S342 that the differential value exceeds the first threshold, the processing shifts to Step S343. At Step S343, the display adjustment unit 308 adjusts display so that the target value of measurement data as an object blinks in blue.

Moreover, when it is determined at Step S342 that the differential value is equal to or smaller than the first threshold, the processing shifts to Step S344. At Step S344, the display adjustment unit 308 determines whether the differential value obtained by the differentiation processing at Step S341 exceeds a second threshold. Here, the first threshold and the second threshold satisfy the relation of first threshold >second threshold.

When it is determined at Step S344 that the differential value is equal to or smaller than the second threshold, the processing shifts to Step S345. At Step S345, the display adjustment unit 308 adjusts display so that the target value of the measurement data blinks in red.

When it is determined at Step S344 that the differential value exceeds the second threshold, the processing shifts to Step S346. At Step S346, the display adjustment unit 308 adjusts display so that the target value of the measurement data is in black.

When the processing at any of Steps S343, S345, and S346 is finished, the processing returns to Step S305 of FIG. 5 and the subsequent processing is performed.

As described above, in the second display adjustment processing, among measurement data displayed in time series, values of measurement data large in change amount in each given time unit blink to be highlighted (blinks in blue or red for display, for example), and the other values of measurement data small in change amount are displayed in the normal state (displayed in black, for example). Generally, when the change amount of measurement data is large, it is highly possible that such measurement data is useful information. Such measurement data is made blink to be highlighted, which allows a user to recognize it strongly.

Moreover, among measurement data large in change amount in each given time unit, a value of measurement data whose change amount is a positive value blinks in blue, while a value of measurement data whose change amount is a negative value blinks in red. In this manner, even when the contents indicated by the measurement data differ depending on whether the change amount is a positive value or a negative value, for example, the difference is highlighted differently, thus allowing a user to recognize it strongly.

Note that although the above description has been given assuming that the first display adjustment processing and the second display adjustment processing are different processing, such processing can be combined by performing scaling of a numerical value of measurement data and then performing threshold determination processing of a differential value obtained from the measurement data in time series, for example. Moreover, the first display adjustment processing and the second display adjustment processing are one example of the display adjustment processing of Step S305 of FIG. 5, and it is also possible to adopt another display adjustment processing for simultaneously displaying specific input data and measurement data in a given display form.

<Display Example of Screen>

(Input Screen)

Figure 8:
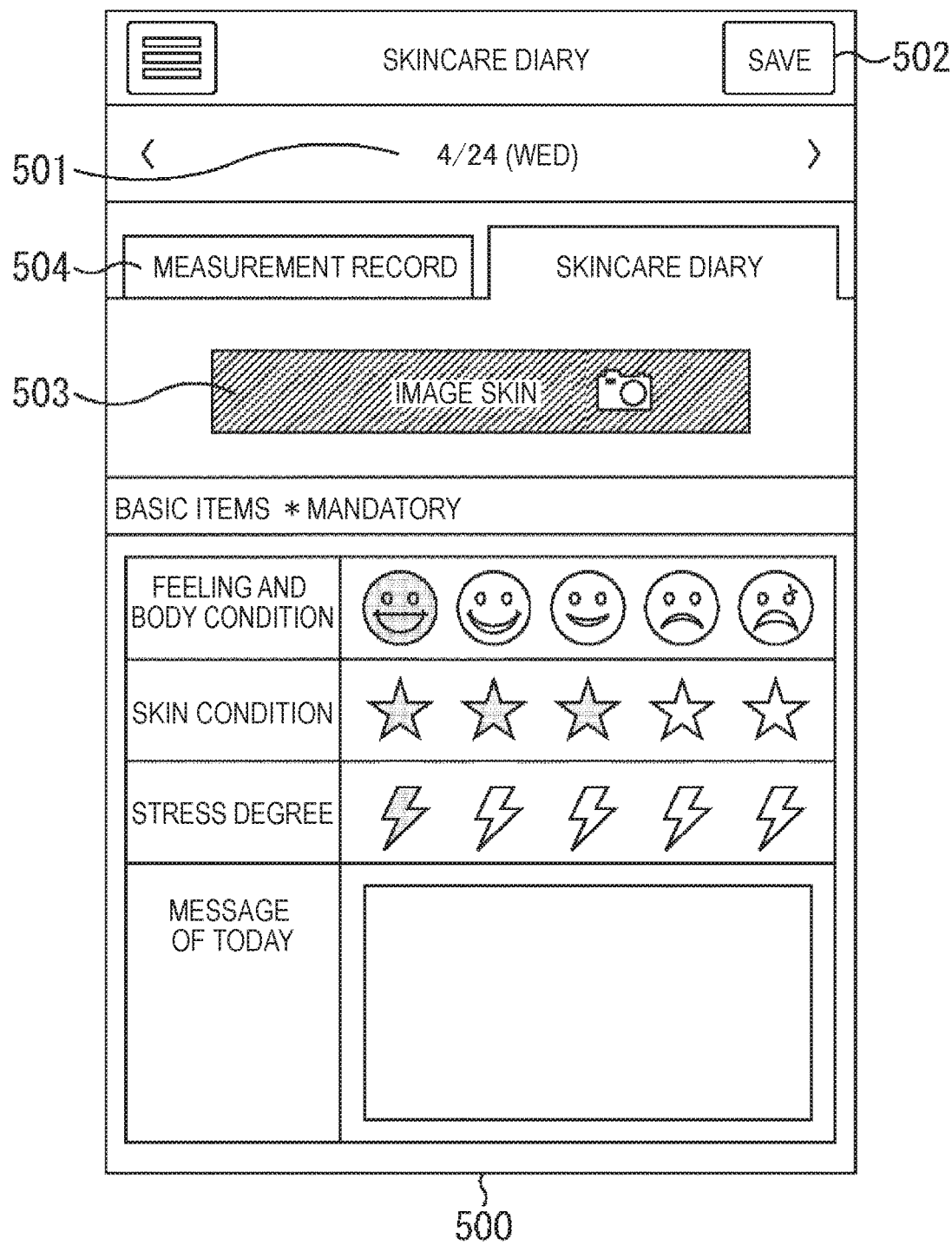
FIG. 8 is a diagram illustrating a display example of an input screen.
Figure 10:
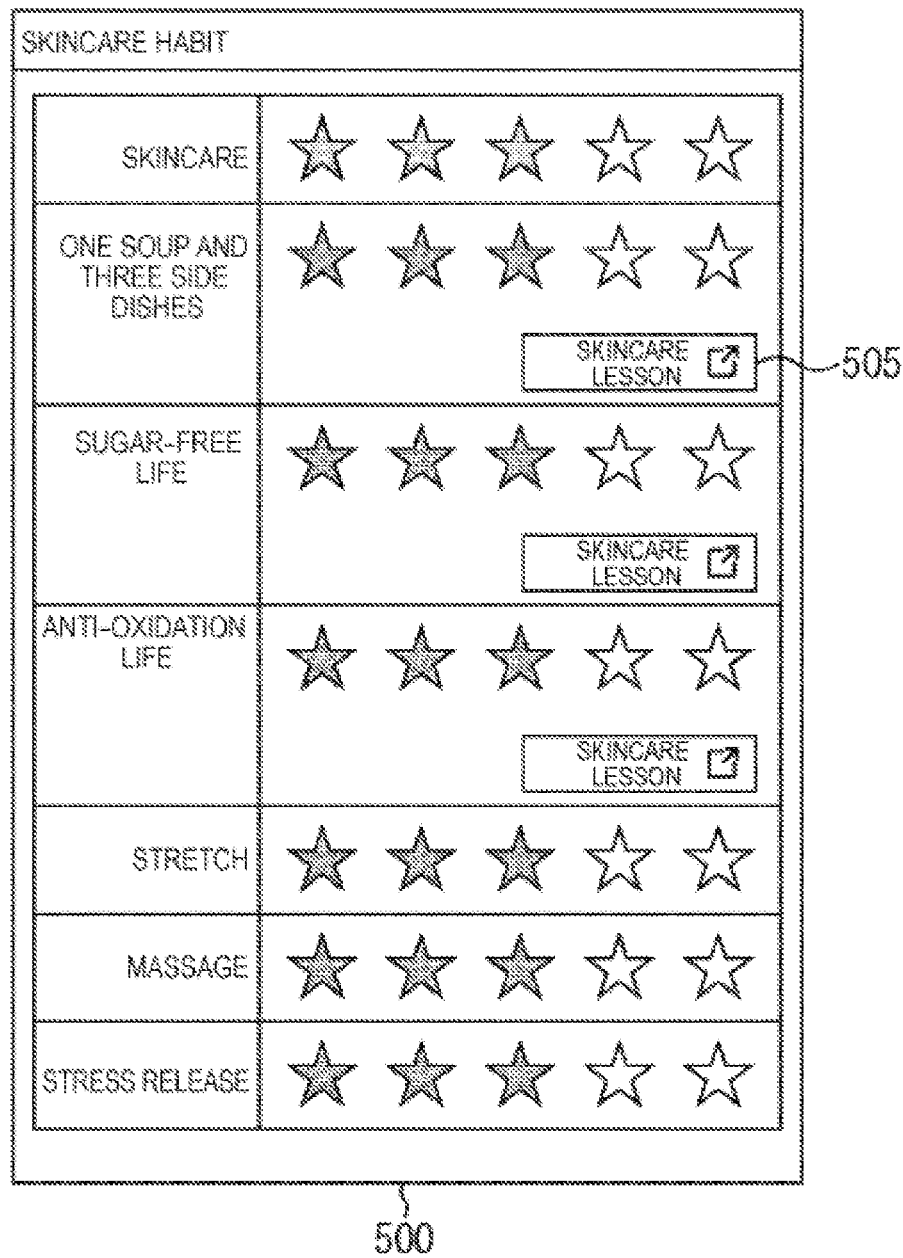
FIG. 10 is a diagram illustrating a display example of an input screen.

FIG. 8 to FIG. 10 illustrate display examples of the input screen 500 displayed on the display unit 121 of the terminal device 10. As described above, when the application for skin analysis has been activated in the terminal device 10 (Step S100 of FIG. 5) and the user has performed given operation, the input screen 500 is displayed on the display unit 121 (Step S101 of FIG. 5).

As illustrated in FIG. 8, a date 501 (e.g., 4/24 (Tue)) is displayed on the input screen 500. Each item displayed on the input screen 500 is input and then a save button 502 is operated, whereby the input data of the date 501 is registered in the analysis server 30. Moreover, the user can image his/her skin by operating an imaging button 503.

For example, when imaging is performed in the state where the camera 201 of the skin measurement instrument 20 is brought close to his/her skin, the measurement data of the date 501 is registered in the analysis server 30. That is, when the user activates the application for skin analysis, inputs his/her state (actual feeling) of the date from the input screen 500, and further images his/her skin state every day, the input data and the measurement data are registered like a diary. Note that the input screen 500 and another screen can be shifted by operating a tab 504.

As illustrated in FIG. 8, basic items that are mandatory items are input first on the input screen 500. For example, in the basic items, "feeling and body condition", "skin condition", and "stress degree" are selected in five grades. Moreover, an arbitrary message can be input as a "message of today".

Moreover, as illustrated in FIG. 9, lifestyle habit is input as arbitrary items on the input screen 500. For example, in the items of lifestyle habit, there are selected or input "sleeping hours" and the "degree of comfortable sleep" thereof, the presence or absence of "meals" and "defecation", and items related to exercise such as the presence or absence of "exercise" and the "type" thereof. Moreover, in addition to the type of "bathing", "menstruation" and "basal body temperature" for women are selected or input.

Moreover, as illustrated in FIG. 10, skincare habit is input as arbitrary items on the input screen 500. For example, in the items of skincare habit, items related to the habit preferable for skin such as "skincare" and "one soup and three side dishes" are selected in five grades. Note that an advice related to a target item can be displayed by operating an operation button 505.

As described above, on the input screen 500, there is displayed the GUI for inputting items related to the lifestyle habit such as sleep, diet, and exercise and the skincare habit such as skincare in addition to the basic items such as feeling and body condition. Thus, the user operates the touch panel 103 to register subjective information (input data) in accordance with the current state of the user regarding each item. Moreover, the user measures his/her skin state using the skin measurement instrument 20 and registers objective information (measurement data) in accordance with his/her skin state. Then, such input data and measurement data are accumulated every day in the analysis server 30 for each user.

Note that when the user performs operation of moving his/her finger from a lower direction to an upper direction while keeping the finger in contact with the surface of the touch panel 103 (so-called swipe operation), the input screen 500 illustrated in FIG. 8 to FIG. 10 is displayed sequentially on the display unit 121. Moreover, the input screen 500 in FIG. 8 to FIG. 10 is one example, and another item may be input in the basic items, the items of lifestyle habit, and the items of skincare habit, or a new item other than the basic items, the items of lifestyle habit, and the items of skincare habit may be provided newly. In short, the contents of input data is arbitrary as long as the input data is subjective information input by the user.

(Analysis Result Screen)

FIG. 11 to FIG. 18 illustrate display examples of the analysis result screen 600 displayed on the display unit 121 of the terminal device 10. As described above, when the application for skin analysis has been activated in the terminal device 10 (Step S100 of FIG. 5) and the user has performed given operation, the analysis result screen 600 is displayed on the display unit 121 (Step S105 of FIG. 5). Here, the description is given assuming that on the analysis result screen 600 of FIG. 11 to FIG. 18, information indicating "pores", "texture", and "stains" is measured as measurement data, information indicating the "degree of comfortable sleep", "feeling and body condition", "bathing", and "basal body temperature" is input as input data, and the correlation between such data is calculated.

Figure 11:
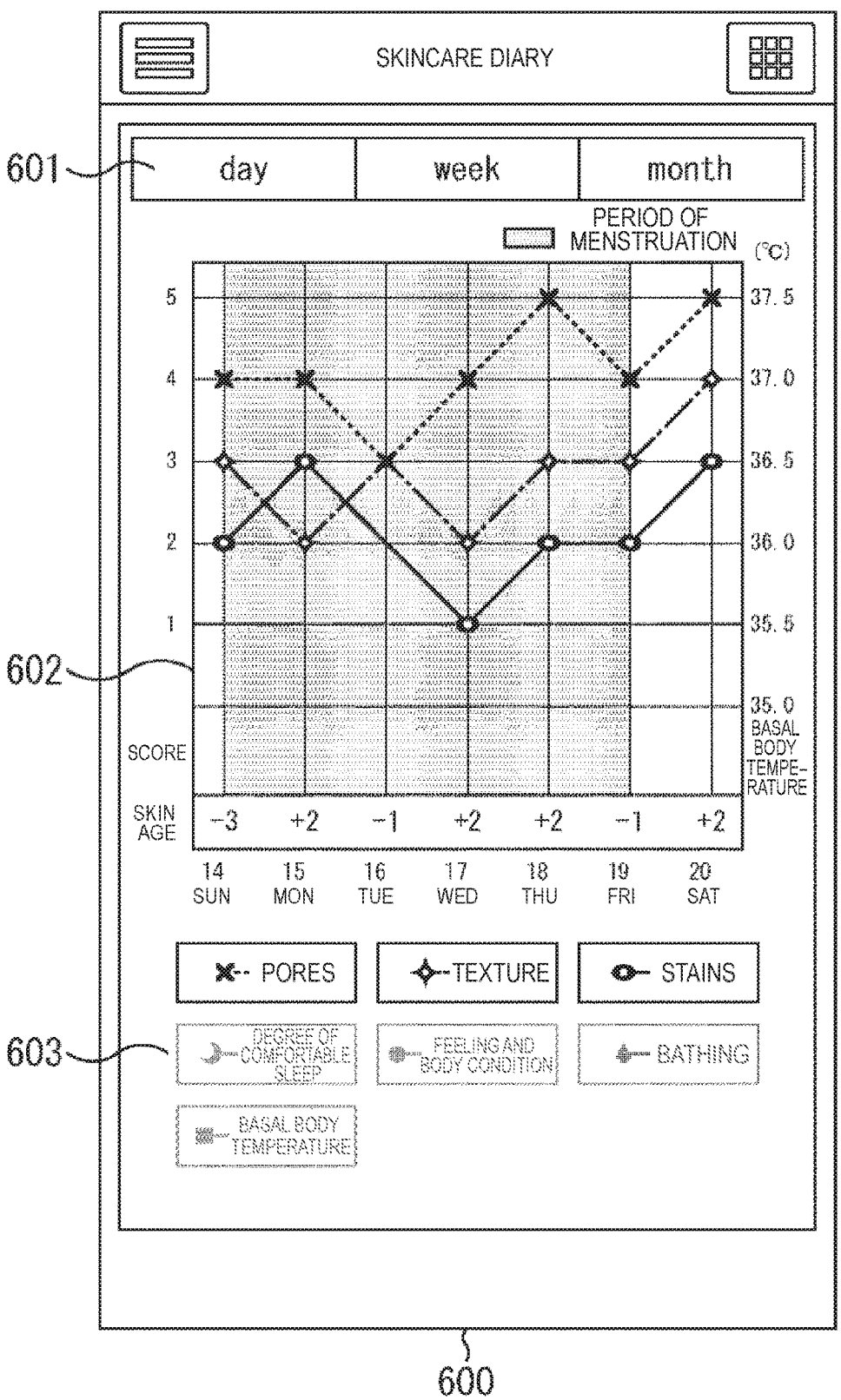
FIG. 11 is a diagram illustrating a display example of an analysis result screen.

The analysis result screen 600 of FIG. 11 illustrates a display example of measurement data such as "pores", "texture", and "stains". On the analysis result screen 600, measurement data can be displayed in a daily unit, a weekly unit, or a monthly unit by operating a tab 601. The analysis result screen 600 of FIG. 11 displays measurement data in a weekly unit from 14th (Sun) to 20th (Sat). Moreover, line graphs corresponding to active items in an item area 603 are displayed on an analysis result display area 602.

That is, the measurement data registered by each user is accumulated in time series in the analysis server 30, and thus analysis using such data and the like is performed, and display data in a display form in accordance with the analysis result is generated. For example, the line graphs of "pores", "texture", and "stains" on the analysis result screen 600 of FIG. 11 display a value for each day of a week in the score of five grades indicated by a vertical axis on the left side of FIG. 11.

Figure 12:
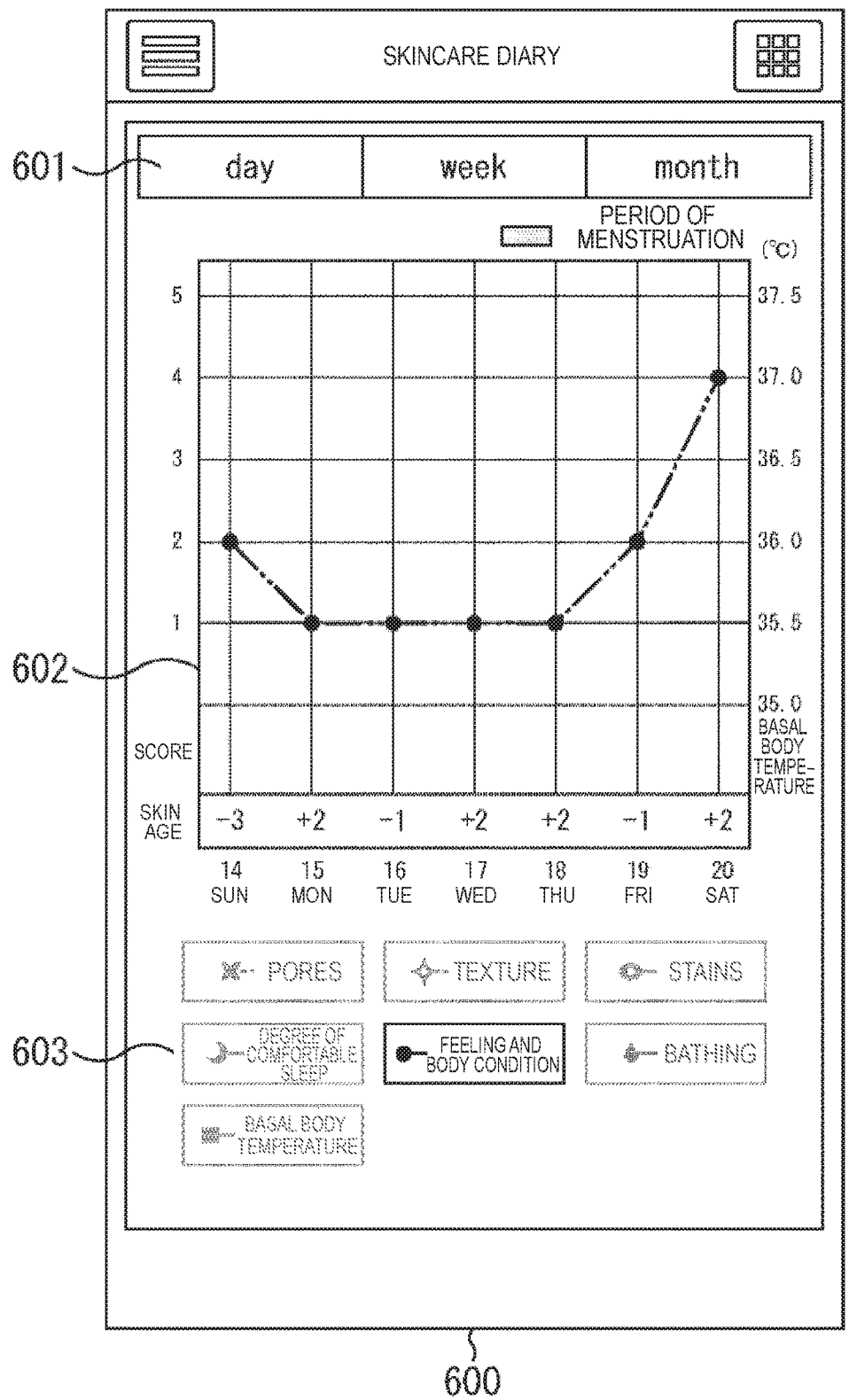
FIG. 12 is a diagram illustrating a display example of an analysis result screen.

Moreover, the analysis result screen 600 of FIG. 12 illustrates a display example of "feeling and body condition" among input data such as the "degree of comfortable sleep", "feeling and body condition", "bathing", and "basal body temperature". That is, the input data registered by each user is accumulated in time series in the analysis server 30, and thus analysis using such input data and the like is performed and display data in a display form in accordance with the analysis result is generated. For example, the line graph of "feeling and body condition" on the analysis result screen 600 of FIG. 12 displays a value for each day of a week in the score of five grades indicated by a vertical axis on the left side of FIG. 12.

Note that values of line graphs of the "degree of comfortable sleep" and "bathing" are also displayed in the score of five grades indicated by the vertical axis on the left side of FIG. 12 although they are not illustrated in the analysis result screen 600 of FIG. 12. Moreover, a line graph of "basal body temperature" is displayed in accordance with a basal body temperature of 35.0° C. to 37.5° C. of a vertical axis on the right side of FIG. 12.

Figure 13:
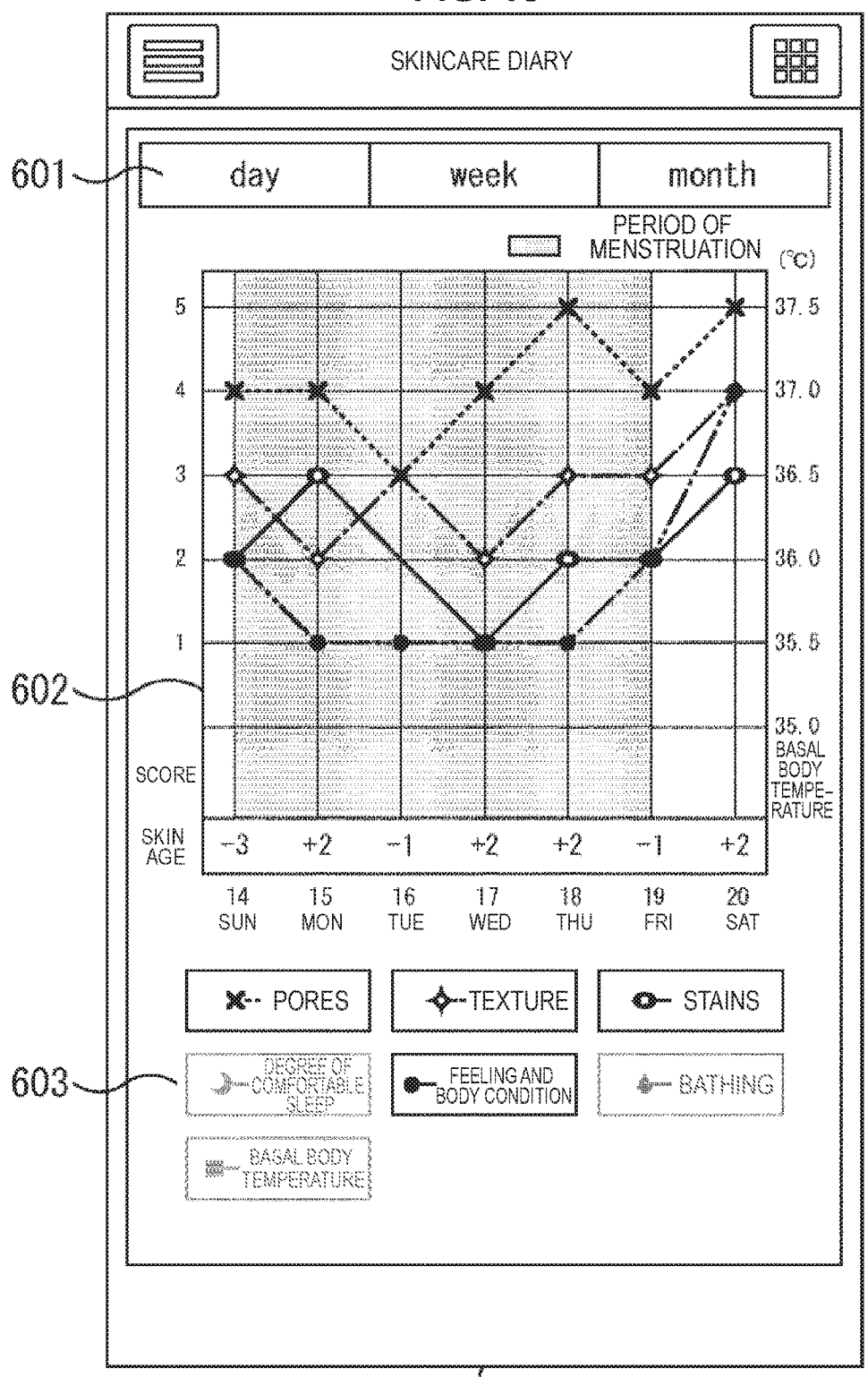
FIG. 13 is a diagram illustrating a display example of an analysis result screen.

The analysis result screen 600 of FIG. 13 illustrates a display example in the case where the measurement data of "pores", "texture", and "stains" and the specific input data of "feeling and body condition" are displayed simultaneously. That is, the input data and the measurement data registered by each user are accumulated in time series in the analysis server 30, and thus analysis of the correlation and the like of such data is performed, and display data in a display form in accordance with the analysis result is generated. For example, on the analysis result screen 600 of FIG. 13, the line graphs of "pores", "texture", and "stains" and "feeling and body condition" represent the score of five grades for each day of a week. Here, the objective measurement data such as "pores" and the subjective input data such as "feeling and body condition" are represented in the same five grades. Thus, user's actual feeling can be associated with the measurement data.

For example, paying attention to the analysis result of 20th (Sat) on the analysis result screen 600 of FIG. 13, the scores of "pores" and "texture" are high scores of 5 points and 4 points, respectively. Here, the score of "feeling and body condition" is also a high score of 4 points. Moreover, paying attention to the analysis result of 17th (Wed), the scores of "texture" and "pores" are low scores of 2 points and 1 point, respectively. Similarly, the score of "feeling and body condition" is also a low score of 1 point.

That is, in addition to the line graphs of the measurement data of "pores", "texture", and "stains", the line graph of "feeling and body condition" as specific input data highest in correlation with such measurement data is displayed, whereby the user can intuitively recognize that the measurement data of his/her skin has relation with his/her feeling and body condition. In this manner, when specific input data highest in correlation with measurement data is extracted among a plurality of pieces of input data and displayed together with the measurement data, it is possible to present useful information to a user, such as the case in which the user can recognize that when his/her feeling and body condition is desirable, the skin state is also desirable.

Figure 14:
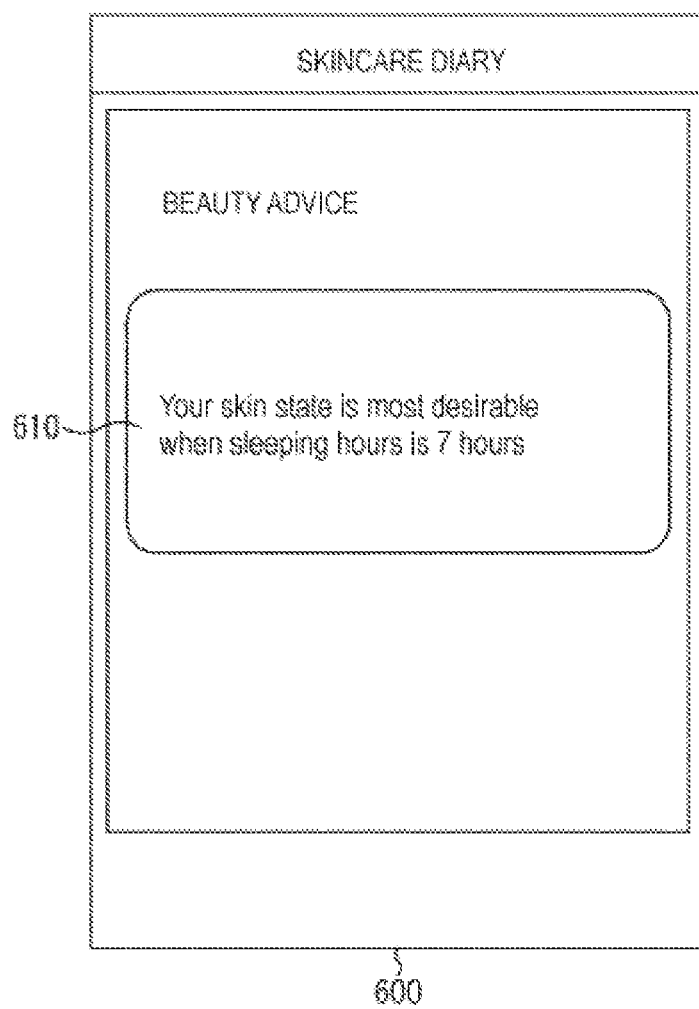
FIG. 14 is a diagram illustrating a display example of an analysis result screen.

The analysis result screen 600 of FIG. 14 illustrates a display example of a value of specific input data in the case where the measurement result indicated by the measurement data indicates the most desirable state. That is, the input data and the measurement data are accumulated in time series in the analysis server 30, and thus the sleeping hours input from the input screen 500 (FIG. 9) when user's skin state indicated by the measurement data is most desirable is extracted as specific input data, and it is displayed as a message. For example, on the analysis result screen 600 of FIG. 14, there is displayed a message 610 "your skin state is most desirable when the sleeping hours is 7 hours" as a beauty advice.

Note that although the analysis result screen 600 of FIG. 14 displays only the message 610, line graphs of measurement data such as "pores" and specific input data such as the "degree of comfortable sleep" may be displayed simultaneously with the message 610.

Figure 15:
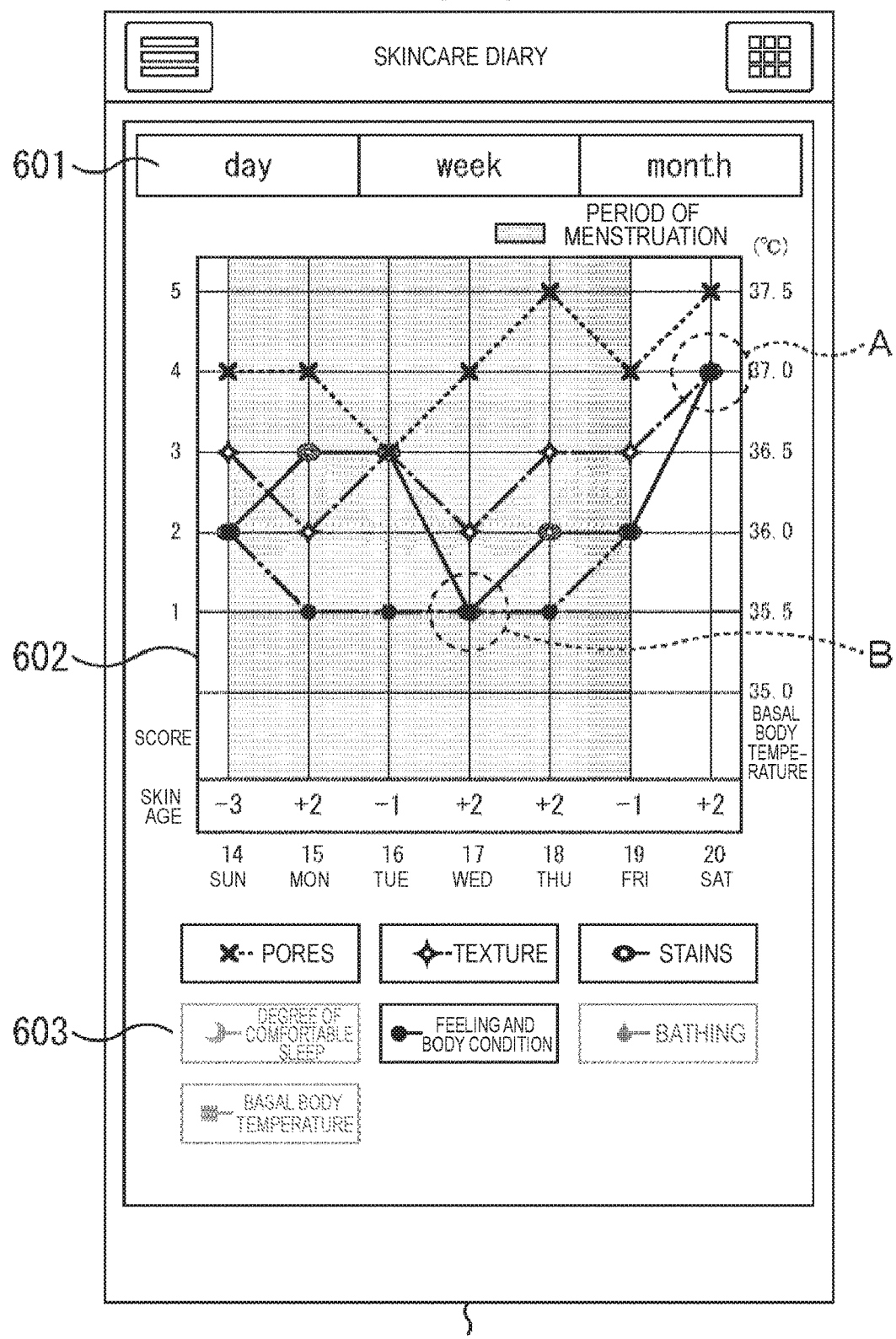
FIG. 15 is a diagram illustrating a display example of an analysis result screen.

The analysis result screen 600 of FIG. 15 illustrates a display example in the case where measurement data large in change amount in a given time unit is highlighted among measurement data in time series. That is, the second display adjustment processing (FIG. 7) is performed in the analysis server 30, whereby a value of measurement data large in change amount in each day can be highlighted among measurement data.

For example, paying attention to measurement data of "stains", the score is considerably increased from 2 points to 4 points during 19th (Fri) and 20th (Sat). In this case, a value of the measurement data of "stains" on 20th (Sat), which is surrounded by a circle A of FIG. 15, is made blink in blue. Meanwhile, in the measurement data of "stains", the score is considerably reduced from 3 points to 1 point during 16th (Tue) to 17th (Wed). In this case, a value of the measurement data of "stains" on 17th (Wed), which is surrounded by a circle B of FIG. 15, is made blink in red.

In this manner, the measurement data large in change amount is highlighted by making it blink in a given color among measurement data in time series, which allows a user to strongly recognize measurement data that is highly possible to be useful information. Moreover, the measurement data large in change amount is highlighted, and values of specific input data are also displayed. Thus, the user can confirm a value of specific input data at a change point of measurement data.

Note that although the description has been given assuming the case where the measurement data large in change amount is highlighted among measurement data in time series on the analysis result screen 600 of FIG. 15, specific input data large in change amount may be highlighted among specific input data in time series.

Figure 16:
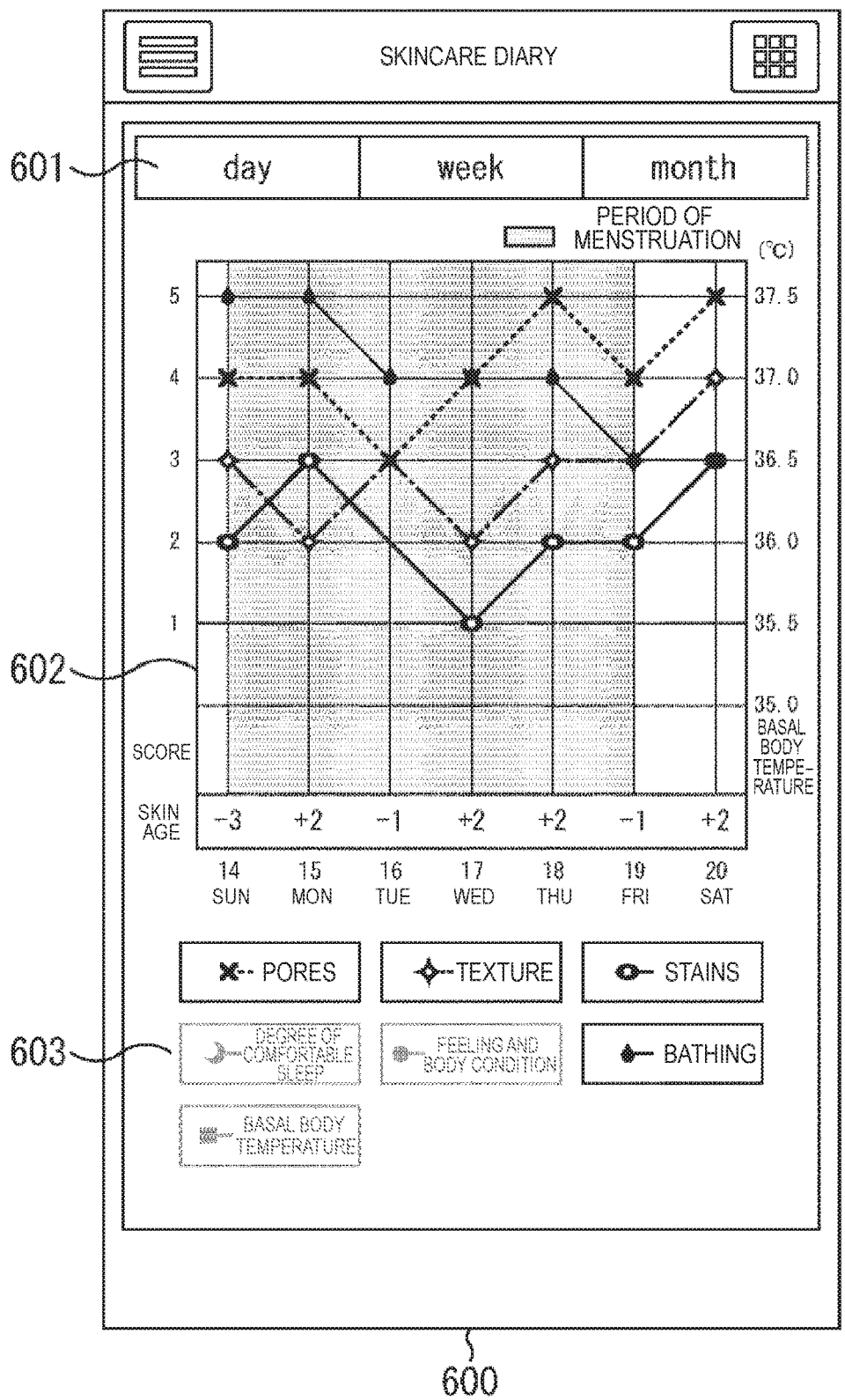
FIG. 16 is a diagram illustrating a display example of an analysis result screen.

The analysis result screen 600 of FIG. 16 illustrates a display example in the case where input data having no correlation with measurement data is displayed. That is, the correlation between input data and measurement data is found in the analysis server 30. Thus, input data having no correlation with the measurement data is extracted as specific input data, and such specific input data having no correlation can be displayed with the measurement data. For example, "bathing" having no correlation with the measurement data such as "pores" is extracted as specific input data to be displayed by a line graph on the analysis result screen 600 of FIG. 16.

In this manner, input data having no (or low) correlation with measurement data is displayed, whereby it is possible to present useful information to a user, such as the case in which a certain user recognizes that the bathing manner does not have influence on the skin state, for example. Note that the analysis server 30 can extract predetermined input data or input data specified by a user as specific input data, and display it together with measurement data.

Figure 17:
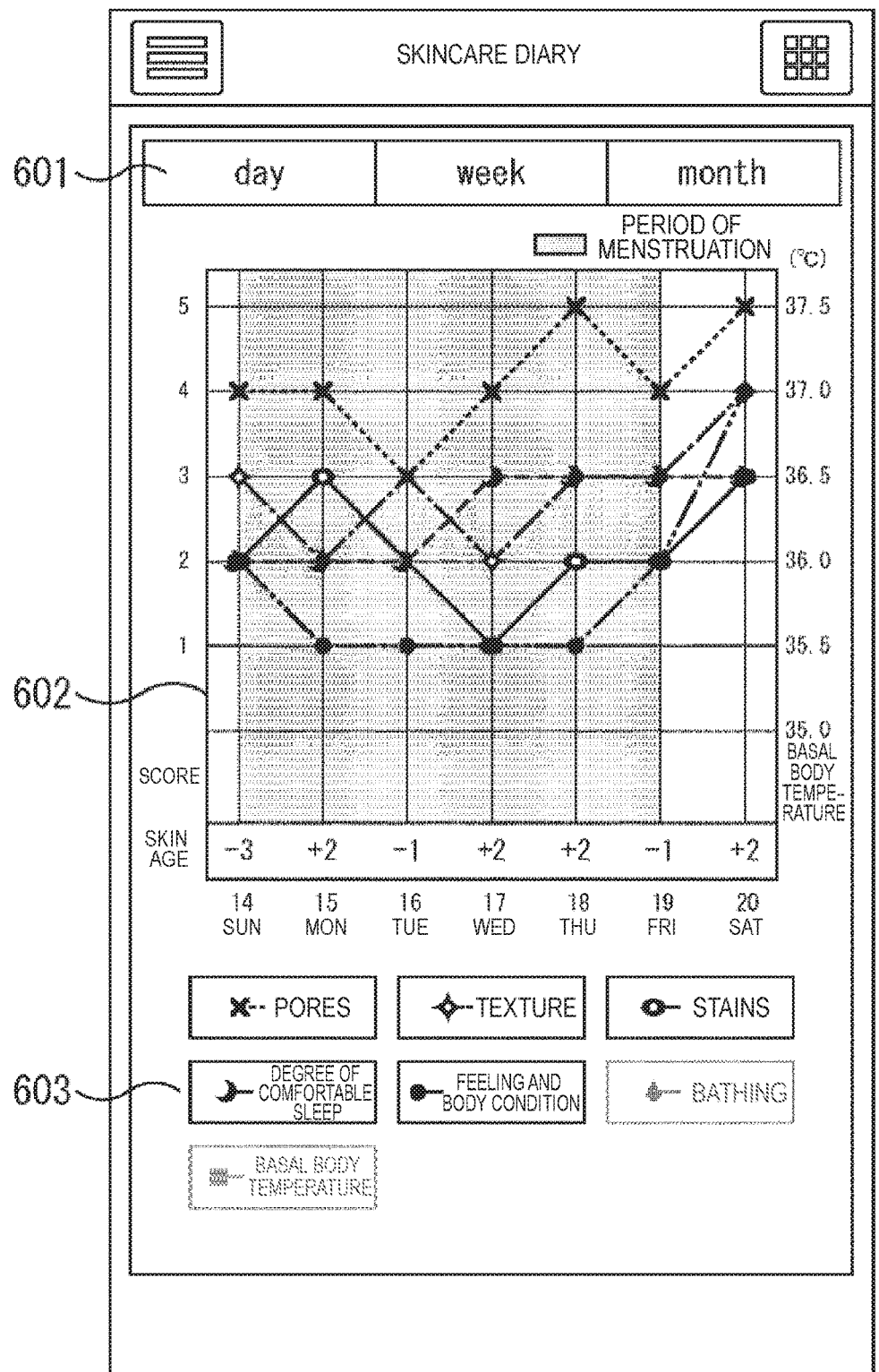
FIG. 17 is a diagram illustrating a display example of an analysis result screen.

The analysis result screen 600 of FIG. 17 illustrates a display example in the case where N pieces (N is an integer equal to or larger than 2) of input data high in correlation with measurement data are displayed. That is, the correlation between input data and measurement data is found in the analysis server 30. Thus, N pieces of input data high in correlation with the measurement data are extracted as specific input data, and the N pieces of specific input data can be displayed with the measurement data. For example, on the analysis result screen 600 of FIG. 17, there are displayed a line graph of "feeling and body condition" highest in correlation and a line graph of the "degree of comfortable sleep" second highest in correlation.

In this manner, a plurality of pieces of specific input data high in correlation with measurement data are displayed, whereby it is possible to present useful information to a user, such as the case in which a certain user recognizes that a plurality of his/her states such as "feeling and body condition" and the "degree of comfortable sleep" have influence on the skin state, for example.

Note that although the description has been given, regarding the analysis result screen 600 of FIG. 17, assuming the case where N pieces of input data higher in correlation are displayed among input data high in correlation with measurement data, N pieces of input data lower in correlation may be displayed. Moreover, among input data low in correlation with measurement data, input data higher or lower in correlation may be displayed, or N pieces of input data having no correlation with measurement data may be displayed.

Figure 18:
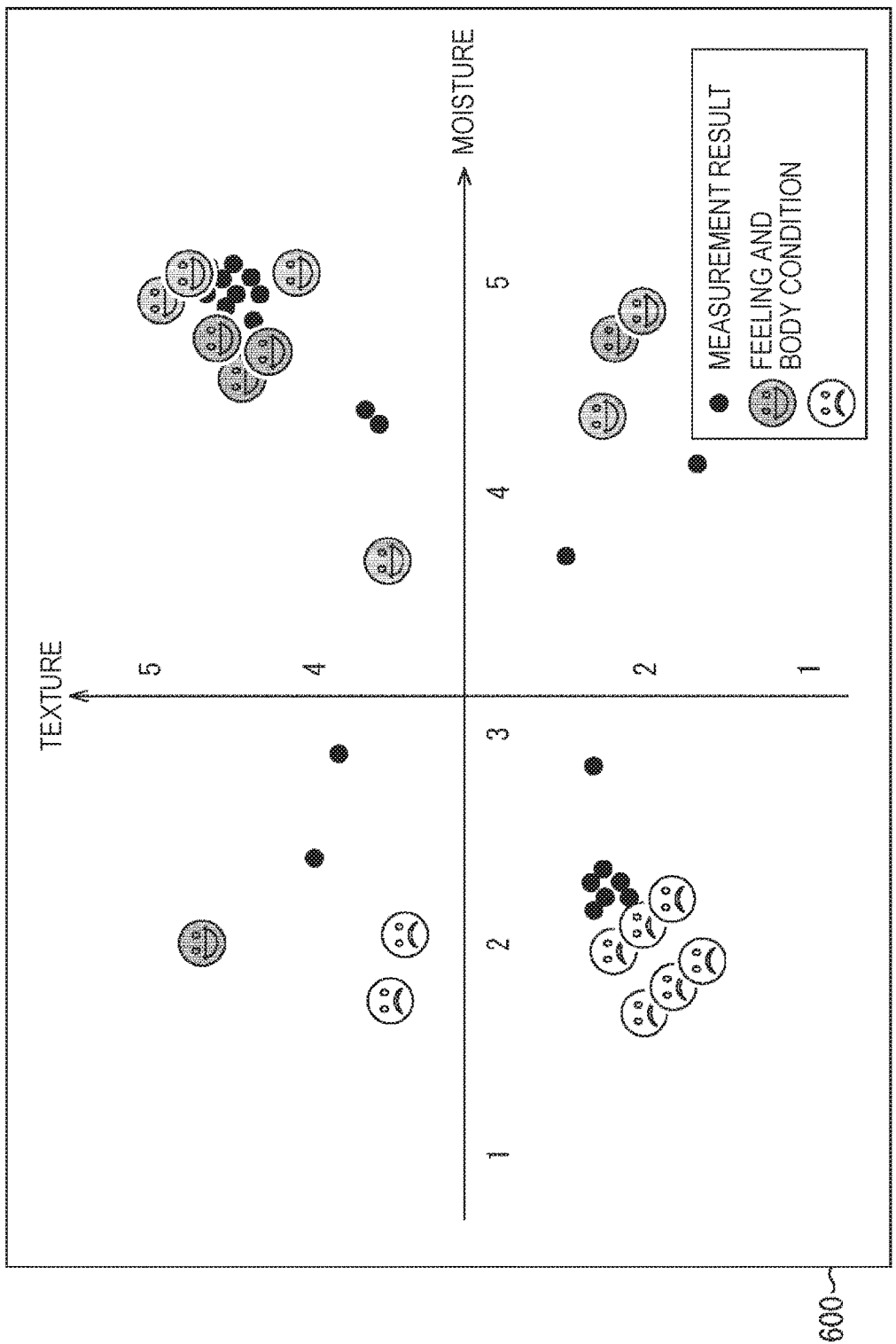
FIG. 18 is a diagram illustrating a display example of an analysis result screen.

Moreover, although the description has been given, regarding the above analysis result screen 600, assuming the case where the specific input data and the measurement data are displayed by line graphs on a plane with a vertical axis indicating score values of such data, and the like and a horizontal axis as a time axis, the display form for simultaneously displaying specific input data and measurement data is not limited thereto. For example, as illustrated in FIG. 18, on the analysis result screen 600, specific input data and measurement data can be also displayed by a scatter diagram with a vertical axis and a horizontal axis indicating score values of such data and the like. For example, on the analysis result screen 600 of FIG. 18, when the scores of measurement data of "texture", "moisture", and the like are high, the score of specific input data of "feeling and body condition" is also high. By contrast, when the scores of measurement data is low, the score of specific input data is also low. Therefore, it is recognized that the user's feeling and body condition have influence on the skin state.

In this manner, the specific input data and the measurement data are displayed by a scatter diagram, which makes it possible to intuitively recognize the distribution of specific input data and measurement data and the correlation. Thus, it is possible to present useful information to the user.

Note that the analysis result screen 600 of FIG. 11 to FIG. 18 is one example, and the analysis result screen 600 may have another display form for simultaneously displaying specific input data and measurement data. For example, on the analysis result screen 600, specific input data and measurement data may be displayed in the first display form when the correlation between the specific input data and the measurement data is positive correlation, while specific input data and measurement data may be displayed in the second display form when the correlation between the specific input data and the measurement data is negative correlation. For example, it is considered that there is positive correlation when long sleeping hours improves a skin state, while there is negative correlation when much stress deteriorates a skin state. In such a case, the display form of specific input data and measurement data is made different in accordance with the kind of the correlation, whereby the user can intuitively distinguish between positive correlation and negative correlation.

<Second Embodiment>
<Configuration of Skin Analysis System>

Figure 19:
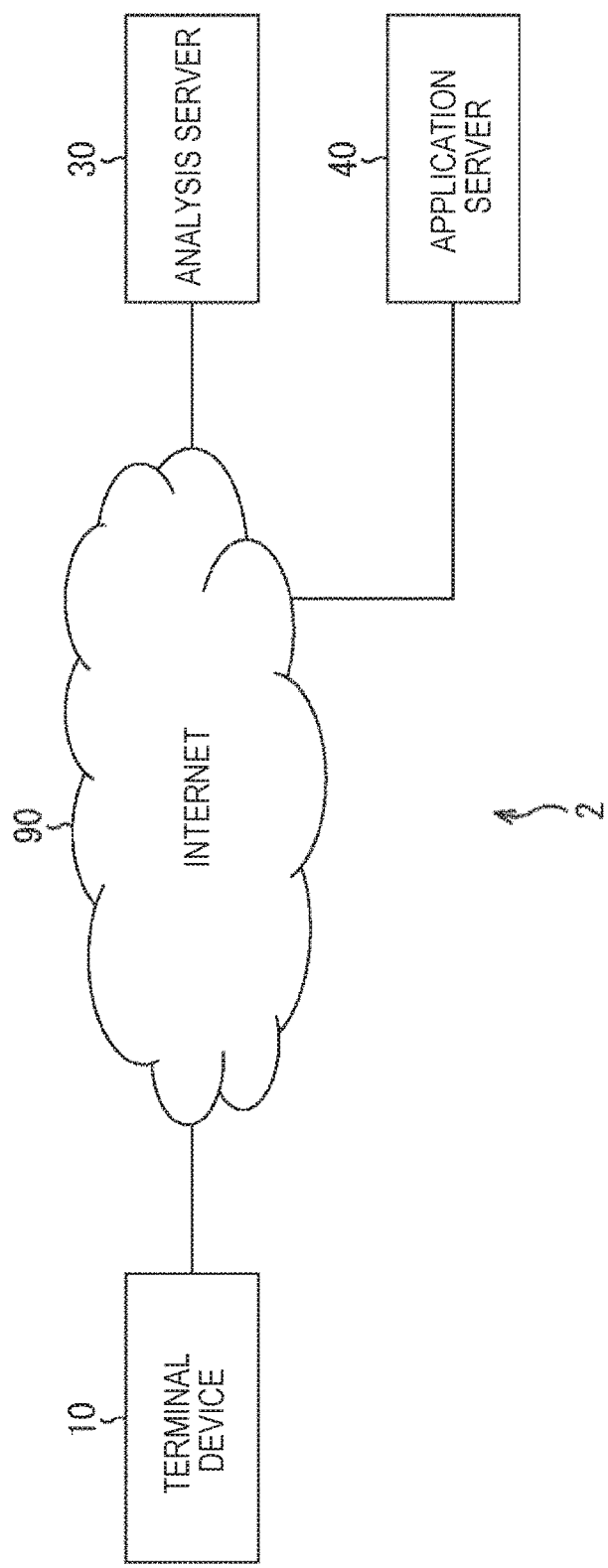
FIG. 19 is a diagram illustrating another configuration of an embodiment of the information processing system to which the present technology is applied.

FIG. 19 is a diagram illustrating another configuration of an embodiment of the information processing system to which the present technology is applied.

A skin analysis system 2 of FIG. 19 is different from the skin analysis system 1 of FIG. 1 in the aspect that the skin measurement instrument 20 is not connected to the terminal device 10. That is, the terminal device 10 of FIG. 19 does not acquire measurement data from the skin measurement instrument 20, and acquires skin measurement data by performing given skin analysis processing using image data obtained by imaging a subject including a user's face with the embedded camera unit 105. Then, the terminal device 10 transmits the input data and the measurement data to the analysis server 30 through the Internet 90, thereby simultaneously displaying the specific input data and the measurement data in a display form in accordance with the analysis result by the analysis server 30.

As described above, the skin analysis system 2 uses the camera unit 105 embedded in the terminal device 10, which saves a user's trouble for preparing the skin measurement instrument 20. Moreover, also in the skin analysis system 2, specific input data and measurement data can be simultaneously displayed in a display form in accordance with an analysis result by the analysis server 30. Thus, it is possible to present useful information to the user.

<Third Embodiment>
<Configuration of Skin Analysis System>

Figure 20:
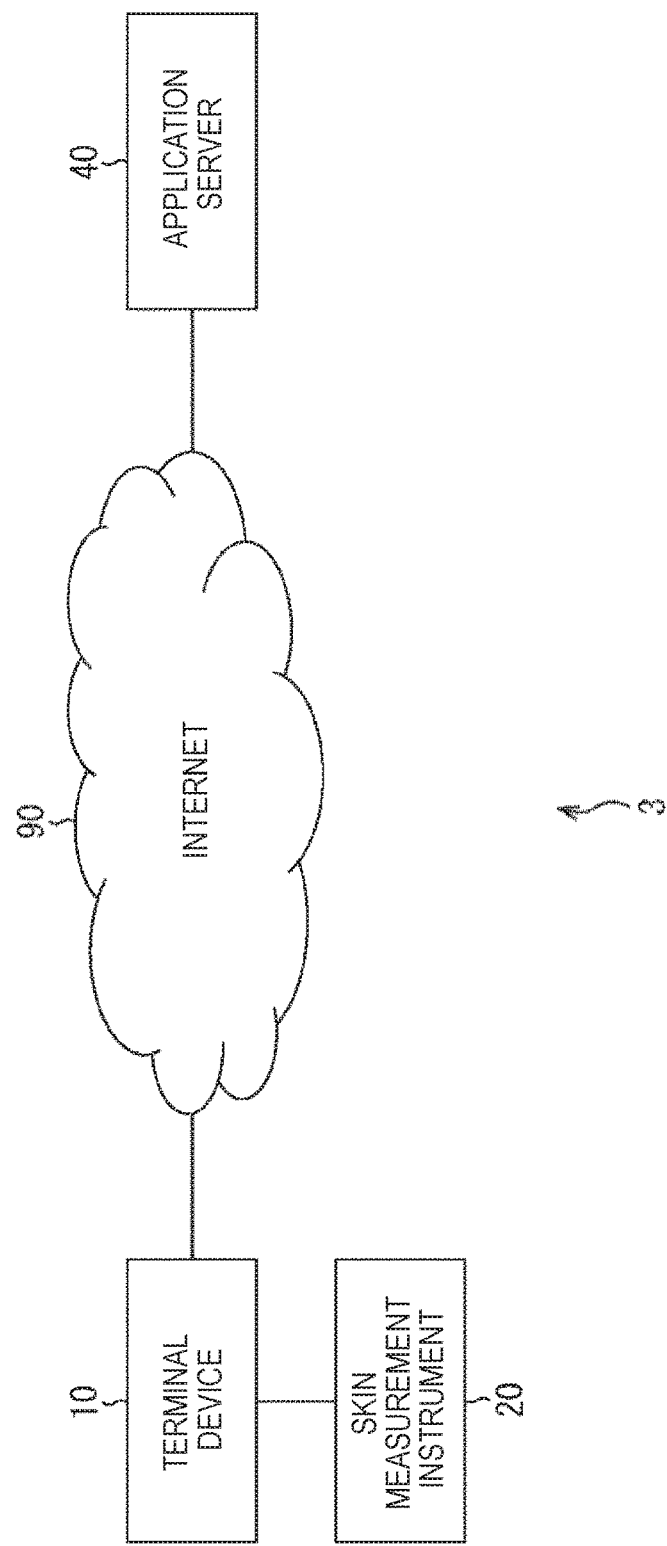
FIG. 20 is a diagram illustrating still another configuration of an embodiment of the information processing system to which the present technology is applied.

FIG. 20 is a diagram illustrating still another configuration of an embodiment of the information processing system to which the present technology is applied.

A skin analysis system 3 of FIG. 20 is different from the skin analysis system 1 of FIG. 1 in the aspect that the analysis server 30 is not connected to the Internet 90. In the skin analysis system 3, the terminal device 10 accesses the application server 40 through the Internet 90 and downloads an application for skin analysis. Then, the terminal device 10 activates the application for skin analysis to perform skin analysis processing.

Here, although the terminal device 10 of FIG. 20 has the configuration illustrated in FIG. 2, it is different in the aspect that the controller 101 has functions of the correlation calculation unit 306, the specific information extraction unit 307, and the display adjustment unit 308 of FIG. 4, and the recording unit 107 has functions of the input data accumulation unit 303, the measurement data accumulation unit 304, and the user data accumulation unit 305 of FIG. 4. With such a configuration, the terminal device 10 of FIG. 20 can analyze input data and measurement data of a user having the terminal device 10 and simultaneously display specific input data and the measurement data in a display form in accordance with the analysis result.

As described above, in the skin analysis system 3, the terminal device 10 solely performs skin analysis processing. Thus, it is possible to rapidly acquire an analysis result without being influenced by loads of the analysis server 30 and the Internet 90. Moreover, also in the skin analysis system 3, specific input data and measurement data can be simultaneously displayed in a display form in accordance with an analysis result by the terminal device 10. Thus, it is possible to present useful information to the user.

Note that in the skin analysis system 3 of FIG. 20, measurement data may be acquired using image data from the camera unit 105 embedded in the terminal device 10 instead of the skin measurement instrument 20, similarly to the skin analysis system 2 of FIG. 19.

As described above, in the present technology, the correlation between a plurality of pieces of input data input by a user and one or more pieces of measurement data obtained as values by measuring the user is found, and at least input data highest in correlation with the measurement data is extracted as specific input data among a plurality of pieces of input data, so as to perform adjustment for simultaneously displaying specific input data and the measurement data. In this manner, the input data indicating the subjective state of the user and the measurement data indicating the objective state of the user are associated, whereby it is possible to present useful information to the user.

Note that although the above description has been given assuming that information of items of lifestyle habit, skincare habit, and the like on the input screen 500 of the application for skin analysis is input as input data, and measurement data of skin is measured as measurement data, the input data and the measurement data are not limited thereto and another kind of input data or another kind of measurement data can be used.

<Description of Computer to which Present Technology is Applied>

The series of processes described above can be executed by hardware but can also be executed by software. When the series of processes is executed by software, a program that constructs such software is installed into a computer. Here, the expression "computer" includes a computer in which dedicated hardware is incorporated and a general-purpose personal computer or the like that is capable of executing various functions when various programs are installed.

Figure 21:
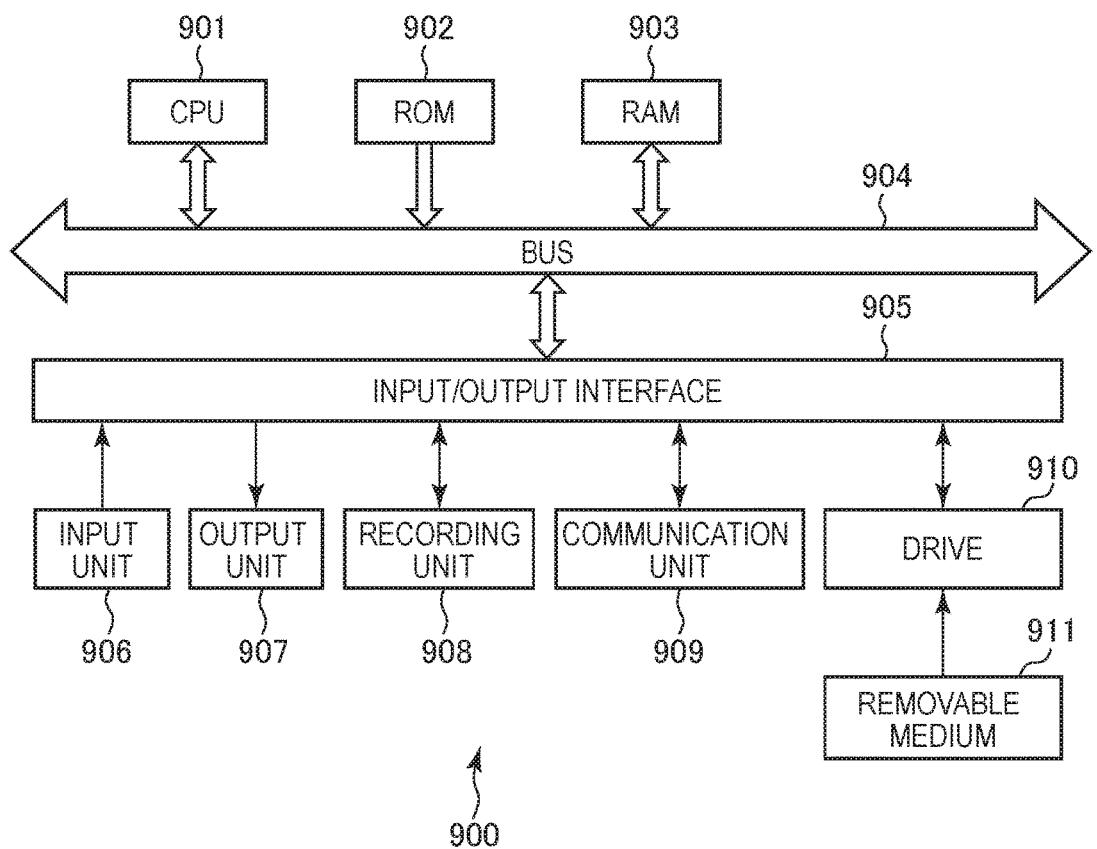
FIG. 21 is a diagram illustrating a configuration example of a computer.

FIG. 21 is a block diagram showing an example configuration of the hardware of a computer that executes the series of processes described earlier according to a program.

In a computer 900, a CPU (Central Processing Unit) 901, a ROM (Read Only Memory) 902, and a RAM (Random Access Memory) 903 are mutually connected by a bus 904. An input/output interface 905 is also connected to the bus 904. An input unit 906, an output unit 907, a recording unit 908, a communication unit 909, and a drive 910 are connected to the input/output interface 905.

The input unit 906 is configured from a keyboard, a mouse, a microphone or the like. The output unit 907 configured from a display, a speaker or the like. The recording unit 908 is configured from a hard disk, a non-volatile memory or the like. The communication unit 909 is configured from a network interface or the like. The drive 910 drives a removable medium 911 such as a magnetic disk, an optical disk, a magneto-optical disk, a semiconductor memory or the like.

In the computer 900 configured as described above, as one example the CPU 901 loads a program stored in the recording unit 908 via the input/output interface 905 and the bus 904 into the RAM 903 and executes the program to carry out the series of processes described earlier.

As one example, the program executed by the computer 900 (the CPU 901) may be provided by being recorded on the removable medium 911 as a packaged medium or the like. The program can also be provided via a wired or wireless transfer medium, such as a local area network, the Internet, or a digital satellite broadcast.

In the computer 900, by loading the removable medium 911 into the drive 910, the program can be installed into the recording unit 908 via the input/output interface 905. It is also possible to receive the program from a wired or wireless transfer medium using the communication unit 909 and install the program into the recording unit 908. As another alternative, the program can be installed in advance into the ROM 902 or the recording unit 908.

Note that the program executed by the computer 900 may be a program in which processes are carried out in a time series in the order described in this specification or may be a program in which processes are carried out in parallel or at necessary timing, such as when the processes are called.

Here, in the present specification, the processing step for describing a program causing the computer 900 to perform various kinds of processing is not necessarily processed in time series along the order illustrated as the flowchart, and may include processing performed in parallel or individually (e.g., parallel processing or processing by an object). Furthermore, the program may be processed by a single computer or may be dispersively processed by a plurality of computers. Moreover, the program may be transferred to a remote computer and then executed.

Further, in the present disclosure, a system has the meaning of a set of a plurality of configured elements (such as an apparatus or a module (part)), and does not take into account whether or not all the configured elements are in the same casing. Therefore, the system may be either a plurality of apparatuses, stored in separate casings and connected through a network, or a plurality of modules within a single casing.

An embodiment of the disclosure is not limited to the embodiments described above, and various changes and modifications may be made without departing from the scope of the disclosure.

For example, the present disclosure can adopt a configuration of cloud computing which processes by allocating and connecting one function by a plurality of apparatuses through a network. Further, each step described by the above-mentioned flow charts can be executed by one apparatus or by allocating a plurality of apparatuses. In addition, in the case where a plurality of processes are included in one step, the plurality of processes included in this one step can be executed by one apparatus or by sharing a plurality of apparatuses.

Additionally, the present technology may also be configured as below.

(1)
An information processing apparatus including:
a correlation calculation unit configured to find correlation between a plurality of pieces of first information input by a user and one or more pieces of second information obtained as values by measuring the user;
a specific information extraction unit configured to extract, as specific first information, at least first information highest in correlation with the second information among the plurality of pieces of first information; and a display adjustment unit configured to perform adjustment for
simultaneously displaying the specific first information and the second information.

(2)
The information processing apparatus according to (1),
wherein the display adjustment unit displays at least a value of the specific first information when a measurement result indicated by the second information indicates a most preferable state.

(3)
The information processing apparatus according to (1) or (2),
wherein the display adjustment unit displays the specific first information and the second information in a first display form when correlation between the specific first information and the second information is positive correlation, and displays the specific first information and the second information in a second display form when the correlation between the specific first information and the second information is negative correlation.

(4)
The information processing apparatus according to any one of (1) to (3),
wherein the display adjustment unit displays the specific first information and the second information in time series.

(5)
The information processing apparatus according to (4),
wherein the display adjustment unit highlights a value of the second information when a change amount in a given time unit of the second information in time series exceeds a given threshold.

(6)
The information processing apparatus according to (5),
wherein the display adjustment unit performs different highlighting between when the change amount of the second information is a positive value and when the change amount of the second information is a negative value.

(7)
The information processing apparatus according to (4),
wherein the display adjustment unit displays a value of the specific first information when a change amount in a given time unit of the second information in time series exceeds a given threshold.

(8)
The information processing apparatus according to (1),
wherein the specific information extraction unit extracts, as the specific first information, first information having no correlation with the second information among the plurality of pieces of first information.

(9)
The information processing apparatus according to (1),
wherein the specific information extraction unit extracts, as the specific first information, N pieces (N is an integer equal to or more than 2) of first information high in correlation with the second information among the plurality of pieces of first information.

(10)
The information processing apparatus according to (9),
wherein the specific first information is N pieces of first information higher or lower in correlation among the plurality of pieces of first information high in correlation with the second information.

(11)
The information processing apparatus according to any one of (8) to (10),
wherein the display adjustment unit displays the specific first information and the second information in time series.

(12)
The information processing apparatus according to (4) or (11),
wherein the display adjustment unit displays the specific first information and the second information by line graphs on a plane with a vertical axis indicating score values of the information and a horizontal axis as a time axis.

(13)
The information processing apparatus according to (1),
wherein the display adjustment unit displays the specific first information and the second information by a scatter diagram with a vertical axis and a horizontal axis indicating score values of the information.

(14)
The information processing apparatus according to any one of (1) to (13),
wherein the specific information extraction unit extracts, as the specific first information, predetermined first information or first information specified by a user among the plurality of pieces of first information.

(15)
The information processing apparatus according to any one of (1) to (14),
wherein the first information is information obtained by inputting a current state of the user, and
wherein the second information is information indicating a measurement result of a skin state of the user.

(16)
The information processing apparatus according to (15), further including:
an input unit configured to input the first information indicating the current state of the user; and a display unit configured to simultaneously display the specific first information indicating the current state of the user and the second information indicating the skin state of the user that are adjusted by the display adjustment unit.

(17)

The information processing apparatus according to (16), further including:

a measurement unit configured to measure the skin state of the user.

(18)

An information processing method of an information processing apparatus, the information processing method including:

by the information processing apparatus, finding correlation between a plurality of pieces of first information input by a user and one or more pieces of second information obtained as values by measuring the user;

extracting, as specific first information, at least first information highest in correlation with the second information among the plurality of pieces of first information; and performing adjustment for simultaneously displaying the specific first information and the second information.

(19)

An information processing system including:

a terminal device;

a measurement device connected to the terminal device; and an information processing apparatus configured to perform communication with the terminal device through a network, wherein the measurement device includes a measurement unit configured to measure a user, wherein the terminal device includes an input unit configured to be operated by the user, and a display unit configured to display various kinds of information, wherein the information processing apparatus includes a correlation calculation unit configured to find correlation between a plurality of pieces of first information input by operation of the user on the input unit and one or more pieces of second information obtained as values by measuring the user by the measurement unit, a specific information extraction unit configured to extract, as specific first information, at least first information highest in correlation with the second information among the plurality of pieces of first information, and a display adjustment unit configured to perform adjustment for simultaneously displaying the specific first information and the second information, and wherein the display unit simultaneously displays the specific first information and the second information that are adjusted by the display adjustment unit.

REFERENCE SIGNS LIST 1, 2, 3 skin analysis system
10 terminal device
20 skin measurement instrument
30 analysis server
40 application server
90 Internet
101 controller
103 touch panel
105 camera unit
108 communication unit
109 connection unit
121 display unit
122 touch sensor
201 camera unit
202 data analysis unit
203 connection unit
301 input data acquisition unit
302 measurement data acquisition unit
303 input data accumulation unit
304 measurement data accumulation unit
305 user data accumulation unit
306 correlation calculation unit
307 specific information extraction unit
308 display adjustment unit
309 display data output unit
311 communication unit
312 accumulation unit
500 input screen
600 analysis result screen
900 computer
901 CPU

The invention claimed is:

1. An information processing apparatus, comprising:
a Central Processing Unit (CPU) configured to:
receive a plurality of pieces of input information that corresponds to a current state of a user, and a measurement result of a skin state of the user;
determine a degree of correlation between the plurality of pieces of input information and the measurement result of the skin state;
extract, as specific input information, at least a first piece of input information from the plurality of pieces of input information, wherein at least the first piece of input information is highest in correlation with the measurement result of the skin state among the plurality of pieces of input information; and
control a display device to:
display the specific input information and the measurement result of the skin state in a first display form based on the degree of correlation, between the specific input information and the measurement result of the skin state, that corresponds to a positive correlation,
wherein the specific input information indicate a preferable state associated with the measurement result of the skin state; and
display the specific input information and the measurement result of the skin state in a second display form based on the degree of correlation, between the specific input information and the measurement result of the skin state, that corresponds to a negative correlation.

2. The information processing apparatus according to claim 1,
wherein the plurality of pieces of input information and the measurement result of the skin state are associated with a time series, and
wherein the CPU is configured to control the display device to concurrently display, in the time series, the specific input information and the measurement result of the skin state based on the degree of correlation between the plurality of pieces of input information and the measurement result of the skin state.

3. The information processing apparatus according to claim 2,
wherein the CPU is further configured to:
obtain a change amount that corresponds to a change in a value of the measurement result of the skin state in the time series; and control the display device to highlight the value of the measurement result of the skin state based on the change amount that exceeds a particular threshold.

4. The information processing apparatus according to claim 2,
wherein the CPU is further configured to:
obtain a change amount that corresponds to a change in a value of the measurement result of the skin state in the time series, wherein the change amount exceeds a particular threshold; and
control the display device to display the value of the specific input information based on the change amount in a particular time unit of the measurement result of the skin state in the time series.

5. The information processing apparatus according to claim 1, wherein the CPU is further configured to extract, as the specific input information, at least a second piece of the plurality of pieces of input information, and wherein the degree of correlation of each of at least the second piece of the plurality of pieces corresponds to no correlation with the measurement result of the skin state.

6. The information processing apparatus according to claim 1, wherein the CPU is further configured to extract, as the specific input information, a set of pieces of input information of the plurality of pieces of input information, and wherein the degree of correlation of each of the set of pieces of input information exceeds a first threshold degree of correlation,
wherein the set of pieces of input information of the plurality of pieces of input information includes at least two pieces of the plurality of pieces of input information.

7. The information processing apparatus according to claim 1, wherein the CPU is further configured to extract, as the specific input information, a set of pieces of input information of the plurality of pieces of input information, and wherein the degree of correlation of each of the set of pieces of input information is less than a second threshold degree of correlation.

8. The information processing apparatus according to claim 7, wherein the CPU is further configured to control the display device to display the specific input information and the measurement result of the skin state in a time series.

9. The information processing apparatus according to claim 1, wherein the CPU is further configured to control the display device to display the specific input information and the measurement result of the skin state by line graphs on a plane,
wherein the line graphs include a vertical axis and a horizontal axis,
wherein the vertical axis indicates score values of the plurality of pieces of input information and the measurement result of the skin state, and
wherein a horizontal axis of the plane corresponds to a time axis.

10. The information processing apparatus according to claim 1, wherein the CPU is further configured to control the display device to display the specific input information and the measurement result of the skin state by a scatter diagram,
wherein the scatter diagram includes a vertical axis and a horizontal axis, and
wherein the horizontal axis indicates score values of the plurality of pieces of input information and the measurement result of the skin state.

11. The information processing apparatus according to claim 1, wherein the CPU is further configured to extract, as the specific input information, one of a second piece of the plurality of pieces of input information or a third piece of the plurality of pieces of input information.

12. The information processing apparatus according to claim 1, wherein the CPU is further configured to control the display device to concurrently display the specific input information and the measurement result of the skin state.

13. A method, comprising:
in an information processing apparatus,
receiving a plurality of pieces of input information that corresponds to a current state of a user, and a measurement result of a skin state of the user;
determining a degree of correlation between the plurality of pieces of input information and the measurement result of the skin state;
extracting, as specific input information, at least a first piece of input information from the plurality of pieces of input information, wherein at least the first piece of input information is highest in correlation with the measurement result of the skin state among the plurality of pieces of input information;
displaying the specific input information and the measurement result of the skin state in a first display form based on the degree of correlation, between the specific input information and the measurement result of the skin state, that corresponds to a positive correlation;
wherein the specific input information indicate a preferable state associated with the measurement result of the skin state; and
displaying the specific input information and the measurement result of the skin state in a second display form based on the degree of correlation, between the specific input information and the measurement result of the skin state, that corresponds to a negative correlation.

14. An information processing system, comprising:
a terminal device;
a measurement device configured to communicate with the terminal device; and
an information processing apparatus configured to communicate with the terminal device via a network,
wherein the measurement device includes a measurement circuitry configured to measure a skin state of a user,
wherein the terminal device includes:
a display device that includes a touch panel configured to:
receive a plurality of pieces of input information that corresponds to a current state of the user;
receive, from the measurement device, a measurement result of the skin state of the user; and
display information based on the plurality of pieces of input information, and
wherein the information processing apparatus includes:
a Central Processing Unit (CPU) configured to:
receive, from the terminal device, the plurality of pieces of input information, and the measurement result of the skin state of the user;
determine a degree of correlation between the plurality of pieces of input information and the measurement result of the skin state of the user;
extract, as specific input information, at least a first piece of input information from the plurality of pieces of input information, wherein at least the first piece of input information is highest in correlation with the measurement result of the skin state of the user among the plurality of pieces of input information; and control the display device to:
display the specific input information and the measurement result of the skin state in a first display form based on the degree of correlation, between the specific input information and the measurement result of the skin state, that corresponds to a positive correlation,
wherein the specific input information indicate a preferable state associated with the measurement result of the skin state of the user; and
display the specific input information and the measurement result of the skin state in a second display form based on the degree of correlation, between the specific input information and the measurement result of the skin state, that corresponds to a negative correlation.

* * * * *